(12) United States Patent
Yanagida et al.

(10) Patent No.: US 10,268,802 B2
(45) Date of Patent: Apr. 23, 2019

(54) MEDICAL IMAGE PROCESSING APPARATUS AND MEDICAL IMAGE PROCESSING SYSTEM

(71) Applicant: TOSHIBA MEDICAL SYSTEMS CORPORATION, Otawara-Shi (JP)

(72) Inventors: Yosuke Yanagida, Otawara (JP); Junichi Tashiro, Otawara (JP); Jyunichi Yoshida, Nasushiobara (JP); Kousuke Sakaue, Nasushiobara (JP); Masashi Yoshida, Nasushiobara (JP); Shigeyuki Ishii, Nasushiobara (JP); Satoshi Ikeda, Yaita (JP); Hitoshi Yamagata, Otawara (JP); Takashi Masuzawa, Otawara (JP); Naoki Sugiyama, Otawara (JP); Muneyasu Kazuno, Nasushiobara (JP)

(73) Assignee: TOSHIBA MEDICAL SYSTEMS CORPORATION, Otawara-Shi (JP)

(*) Notice: Subject to any disclaimer, the term of this patent is extended or adjusted under 35 U.S.C. 154(b) by 0 days.

(21) Appl. No.: 14/635,086

(22) Filed: Mar. 2, 2015

(65) Prior Publication Data
US 2015/0261915 A1    Sep. 17, 2015

(30) Foreign Application Priority Data
Mar. 11, 2014 (JP) ................................. 2014-048083

(51) Int. Cl.
*G06F 19/00* (2018.01)
*G06F 17/24* (2006.01)
(Continued)

(52) U.S. Cl.
CPC .......... *G06F 19/321* (2013.01); *G06F 17/241* (2013.01); *G06F 17/30268* (2013.01);
(Continued)

(58) Field of Classification Search
CPC ............ G06F 19/3487; G06F 19/3437; G06F 19/345; G06F 17/241; G06F 3/0484;
(Continued)

(56) References Cited

U.S. PATENT DOCUMENTS

| 7,646,898 B1* | 1/2010 | Nowinski | G06T 7/0012 |
| | | | 382/128 |
| 2004/0151358 A1* | 8/2004 | Yanagita | G06F 19/321 |
| | | | 382/132 |

(Continued)

FOREIGN PATENT DOCUMENTS

| JP | 2005-80969 | 3/2005 |
| JP | 2006-181146 A | 7/2006 |

(Continued)

OTHER PUBLICATIONS

Office Action dated Oct. 9, 2018 in Japanese Patent Application No. 2015-35621.

*Primary Examiner* — Kenny A Cese
(74) *Attorney, Agent, or Firm* — Oblon, McClelland, Maier & Neustadt, L.L.P.

(57) ABSTRACT

According to one embodiment, a medical image processing apparatus and a medical image processing system includes at least a position detecting unit, a human body chart storage unit, a mapping chart generating unit, and a display. A position detecting unit detects a position of a characteristic local structure in a human body from the medical image. A human body chart storage unit stores a human body chart that represents the human body. A mapping chart generating unit generates a mapping chart that is the human body chart to which a mark indicating a position of the local structure detected by the position detecting unit is added. A display displays the mapping chart.

17 Claims, 22 Drawing Sheets

(51) Int. Cl.
*G06F 17/30* (2006.01)
*G06T 15/00* (2011.01)
*G06T 11/20* (2006.01)
*G06T 19/00* (2011.01)

(52) U.S. Cl.
CPC ............ *G06F 19/00* (2013.01); *G06T 11/206* (2013.01); *G06T 15/00* (2013.01); *G06T 19/00* (2013.01); *G06T 2210/41* (2013.01); *G06T 2219/00* (2013.01)

(58) Field of Classification Search
CPC ............ G06F 17/30268; G06F 3/0482; G06F 3/0487; G06F 17/30696; G06F 3/0481; G06F 3/04842; A61B 19/50; A61B 8/468; A61B 2019/505; A61B 19/56; A61B 8/483; A61B 2090/3966; A61B 6/469; A61B 8/466; A61B 8/5223; G06K 9/469; G06T 7/0012; G06T 2207/10081; G06T 19/00; G06T 2207/30004; G06T 2200/04; G06T 11/206; G06T 17/00; G06T 19/20; G06T 2200/24; G06T 15/00; G06T 7/00
See application file for complete search history.

(56) References Cited

U.S. PATENT DOCUMENTS

| | | | | |
|---|---|---|---|---|
| 2005/0256389 A1* | 11/2005 | Koga | ............ | A61B 5/103 600/407 |
| 2005/0283053 A1* | 12/2005 | deCharms | ............ | A61B 5/055 600/300 |
| 2006/0050943 A1* | 3/2006 | Ozaki | ............ | A61B 6/032 382/131 |
| 2009/0070140 A1* | 3/2009 | Morsch | ............ | G06F 19/3487 705/2 |
| 2012/0050330 A1* | 3/2012 | Iizuka | ............ | A61B 6/5235 345/641 |
| 2013/0035957 A1* | 2/2013 | Gossler | ............ | A61B 5/055 705/3 |
| 2013/0111387 A1* | 5/2013 | Li | ............ | G06Q 50/24 715/771 |
| 2013/0290826 A1* | 10/2013 | Niwa | ............ | G06F 19/321 715/230 |
| 2014/0219500 A1* | 8/2014 | Moehrle | ............ | G06F 19/321 382/103 |
| 2014/0229890 A1* | 8/2014 | Tokunaga | ............ | A61B 6/00 715/786 |

FOREIGN PATENT DOCUMENTS

| | | | | |
|---|---|---|---|---|
| JP | 2008-43524 | | 2/2008 | |
| JP | 2008-73397 | | 4/2008 | |
| JP | 2009-342 A | | 1/2009 | |
| JP | 2012-71122 A | | 4/2012 | |
| JP | 5138431 | | 2/2013 | |
| JP | WO 2013046940 A1 * | | 4/2013 | ............ A61B 6/00 |
| JP | 5197029 | | 5/2013 | |
| WO | WO 2009/104510 A1 | | 8/2009 | |

\* cited by examiner

FIG. 5A

| HEAD, NECK |
|---|
| ANTERIOR ARCH (TUBERCLE) OF ATLAS (CERVICAL VERTEBRA I) |
| SUPERIOR TIP OF DENS / PEG (CERVICAL VERTEBRA II) |
| SUPERIOR ASPECT OF RIGHT EYE GLOBE |
| SUPERIOR ASPECT OF LEFT EYE GLOBE |
| CENTER OF RIGHT EYE GLOBE |
| CENTER OF LEFT EYE GLOBE |
| ⋮ |

FIG. 5B

| CHEST |
|---|
| BIFURCATION OF TRACHEA |
| APEX OF RIGHT LUNG |
| APEX OF LEFT LUNG |
| INFERIOR ANGLE OF RIGHT SCAPULA |
| INFERIOR ANGLE OF LEFT SCAPULA |
| START OF LEFT SUBCLAVIAN ARTERY (BRANCHING OFF AORTIC ARCH) |
| ⋮ |

FIG. 5C

| ABDOMEN |
|---|
| SUPERIOR POLE OF RIGHT KIDNEY |
| SUPERIOR POLE OF LEFT KIDNEY |
| INFERIOR POLE OF RIGHT KIDNEY |
| INFERIOR POLE OF LEFT KIDNEY |
| HEAD OF PANCREAS |
| TIP OF TAIL OF PANCREAS |
| ⋮ |

FIG. 5D

| LOWER LIMBS |
|---|
| LATERAL EPICONDYLE OF RIGHT FEMUR |
| MEDIAL EPICONDYLE OF RIGHT FEMUR |
| LATERAL EPICONDYLE OF LEFT FEMUR |
| MEDIAL EPICONDYLE OF LEFT FEMUR |
| LATERAL CONDYLE OF RIGHT TIBIA |
| MEDIAL CONDYLE OF RIGHT TIBIA |
| ⋮ |

| IDENTIFIER | NAME | RELIABILITY | SITE | BODY TISSUE | PATIENT COORDINATE SYSTEM | | |
|---|---|---|---|---|---|---|---|
| | | | | | X | Y | Z |
| ABD025.C | CENTER OF BODY OF L5 | 0.87 | ABDOMEN | SKELETAL SYSTEM | -3.1 | 23.4 | 90.0 |
| ABD032.C | SUPERIOR ASPECT OF RIGHT ILIAC SPINE | 0.82 | ABDOMEN | SKELETAL SYSTEM | -11.1 | -54.4 | 84.1 |
| ABD039.C | SUPERIOR ASPECT OF LEFT ILIAC SPINE | 0.83 | ABDOMEN | SKELETAL SYSTEM | -3.0 | 30.0 | 104.0 |
| ⋮ | ⋮ | ⋮ | ⋮ | ⋮ | ⋮ | ⋮ | ⋮ |

| ANATOMICAL POSITION | VOXEL COORDINATES | | |
|---|---|---|---|
| | X | Y | Z |
| AL1 | Xa1 | Ya1 | Za1 |
| AL2 | Xa2 | Ya2 | Za2 |
| AL3 | Xa3 | Ya3 | Za3 |
| AL4 | Xa4 | Ya4 | Za4 |
| AL5 | Xa5 | Ya5 | Za5 |

| ANATOMICAL POSITION | ANATOMICAL CHART COORDINATES | |
|---|---|---|
| | X | Y |
| AL1 | Xb1 | Yb1 |
| AL2 | Xb2 | Yb2 |
| AL3 | Xb3 | Yb3 |
| AL4 | Xb4 | Yb4 |
| AL5 | Xb5 | Yb5 |

| ANATOMICAL | VOXEL COORDINATES | | |
| --- | --- | --- | --- |
| POSITION | X | Y | Z |
| AL1 | Xa1 | Ya1 | Za1 |
| AL2 | Xa2 | Ya2 | Za2 |
| AL3 | Xa3 | Ya3 | Za3 |
| AL4 | Xa4 | Ya4 | Za4 |

MEDICAL IMAGE PROCESSING APPARATUS AND MEDICAL IMAGE PROCESSING SYSTEM

CROSS-REFERENCE TO RELATED APPLICATIONS

This application claims the benefit of priority of Japanese Patent Application No. 2014-048083, filed Mar. 11, 2014, the entire contents of which are incorporated herein by reference.

FIELD

Embodiments described herein relate generally to a medical image processing apparatus and a medical image processing system.

BACKGROUND

Various inspection devices (referred to as modality devices, hereinafter) used in image diagnosis are essential in the modern medicine, because those inspection devices can perform minimally invasive inspection of a human body. Advances in performance of the modality devices have allowed a quality image of high resolution to be obtained and accurate and precise inspection to be achieved in image diagnosis. For example, a computed tomography (CT) apparatus can obtain high-resolution three-dimensional information on a tissue inside an object, and a magnetic resonance imaging (MRI) apparatus can perform imaging in various ways depending on the modality device, such as an MR angiography (MRA) that images fresh blood containing no contrast medium by MRI. With advances in medical image digitalization, a hospital information system (HIS) that is an ordering system that processes a request from a doctor via an electronic network, a radiology information system (RIS) and a picture archiving and communication system (PACS) that accumulates images obtained by the modality device as electronic data have been developed.

Advances of the modality devices have enabled easy and detailed observation of the inside of a living body. An enormous amount of data can be obtained, and many modality devices obtain data in the form of volume data composed of a plurality of images. The amount of volume data is no less than thousands of images when a whole body is imaged, and it is burdensome to a doctor or the like who performs radiological interpretation of these data to make a diagnosis. Radiological interpretation is an important task for diagnosis of a disease or determination of a treatment plan. It is not easy to analyze the enormous amount of medical images to make an early decision, although there is a demand for early detection. In view of such circumstances, as inventions for supporting image diagnosis, there have been proposed a radiological interpretation report creating apparatus that identifies an abnormal anatomical site and determines the degree of malignancy of the site by using a segmentation technique or the like (see Patent Literature 1, for example) and an image analyzing apparatus (see Patent Literature 2, for example) that determines a positional correspondence between images obtained in two different inspections.

Radiological interpretation and diagnosis need to be accurate, and to make an accurate diagnosis, an abnormal site or a site to be treated in the obtained medical image needs to be precisely grasped. However, to read an anatomical site from a medical image requires technical expertise. In view of this, techniques of representing or constructing an anatomical position in a human body through a mathematical approach have been studied and provided.

The "anatomical position" refers to a characteristic local structure in a human body (referred to as a local structure, hereinafter) that is important for understanding a medical image and serves as a mark when the human body is anatomically mapped. For example, an anterior arch (node) of a first cervical vertebra (cervical vertebra I) of a head is a local structure, a bifurcation of trachea in a chest is also a local structure, and an upper pole of a right kidney or the like in an abdomen is also a local structure. The position of the local structure (anatomical position) is automatically detected from the medical image obtained by the modality device, such as the X-ray CT device or the MRI device, by common image analysis, pattern recognition technique or the like.

In radiological interpretation, the position of the anatomical site displayed in the medical image needs to be correctly recognized. However, to identify an anatomical site or the position thereof in the obtained image requires technical expertise including knowledge and experience. In some cases, an enormous amount of data containing hundreds or thousands of medical images, such as volume data, is obtained per person in one X-ray CT or MRI imaging, and creation of a radiological interpretation report is a significant burden in image diagnosis. If hundreds or thousands of images are obtained, it is troublesome to find a required image, or more specifically, to find which image includes a desired anatomical site, which image has been selected as a representative image (referred to as a key image, hereinafter) which includes a finding, or in which image a mark (referred to as an annotation, hereinafter) is imparted to a particular position of interest.

The obtained medical image is stored in the PACS or the like as electronic data. The medical image data stored in the storage device is associated with various kinds of information on an inspection or a patient. Anatomical site information included in the retained medical image data may be recorded in any of information concerning an inspection or a patient. However, such a task is manually performed by an inspection technician, a radiologist or the like. In addition, such recording may not be performed, and specific details cannot be recorded. Therefore, to check what anatomical site is included in the retained medical image data, it is necessary to display the medical image data on a medical image display apparatus or the like and visually check the medical image data.

In view of such circumstances, there is a demand for a medical image processing apparatus that helps checking a content of a medical image based on the position (anatomical position) of the local structure described above.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5A shows examples of local structures of a head and a neck;

FIG. 5B shows, as local structures of a chest, a bifurcation of trachea, an apex of a right lung, an apex of a left lung, an inferior angle of a right scapula, an inferior angle of a left scapula and an origin of a left subclavian artery;

FIG. 5C shows, as local structures of an abdomen, an upper pole of a right kidney, an upper pole of a left kidney, a lower pole of a right kidney, a lower pole of a left kidney, a head of a pancreas and a tip of a tail of a pancreas;

FIG. 5D shows, as local structures of lower limbs, a lateral epicondyle of a right femur, a medial epicondyle of a right femur, a lateral epicondyle of a left femur, a medial epicondyle of a left femur, a lateral condyle of a right tibia and a medial condyle of a right tibia;

DETAILED DESCRIPTION

Hereinbelow, a description will be given of a medical image processing apparatus and a medical image processing system according to embodiments of the present invention with reference to the drawings.

Medical image processing apparatuses according to embodiments have a function of displaying a medical image for a radiological interpretation report creation apparatus, a medical image observation apparatus (image viewer) or the like.

In general, according to one embodiment, a medical image processing apparatus includes a position detecting unit, a human body chart storage unit, a mapping chart generating unit, and a display. A position detecting unit detects a position of a characteristic local structure in a human body from the medical image. A human body chart storage unit stores a human body chart that represents the human body. A mapping chart generating unit generates a mapping chart that is the human body chart to which a mark indicating a position of the local structure detected by the position detecting unit is added. A display displays the mapping chart.

(1) Configuration

Figure 1:
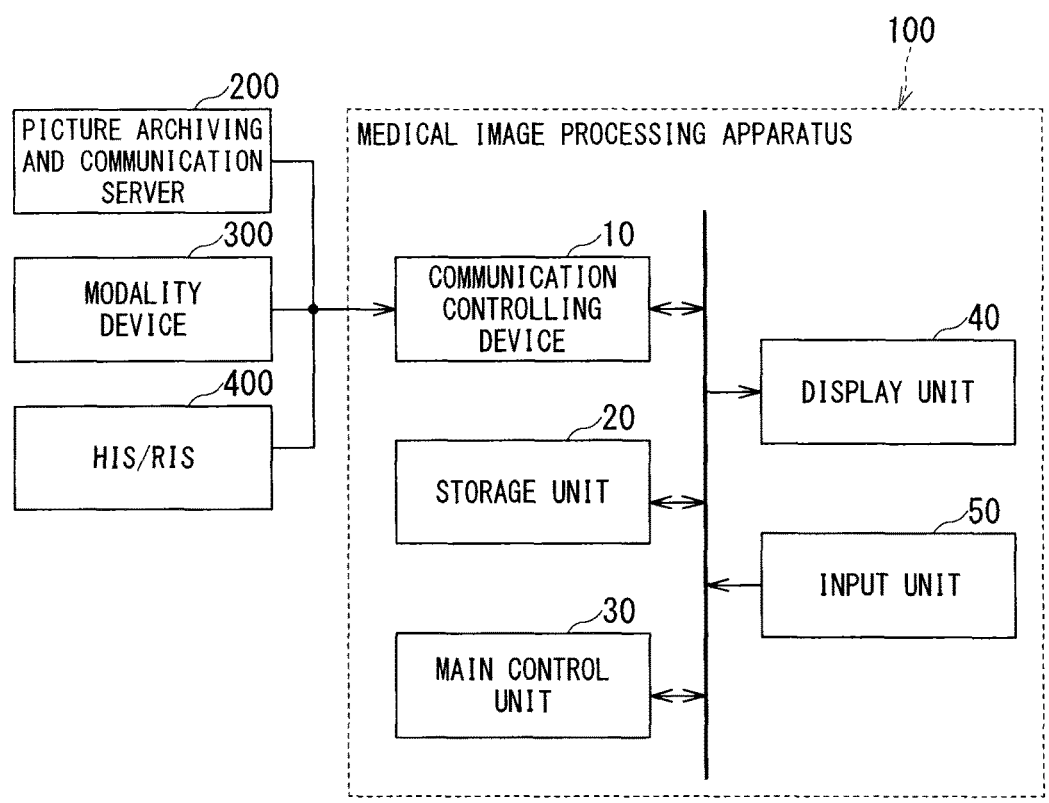
FIG. 1 is a conceptual diagram showing an example of a medical image processing apparatus according to an embodiment.

FIG. 1 is a conceptual diagram showing an example of a medical image processing apparatus 100 according to an embodiment. As shown in FIG. 1, the medical image processing apparatus 100 comprises a communication controlling device 10, a storage unit 20, a main control unit 30, a display unit 40 and an input unit 50. The medical image processing apparatus 100 is connected to a picture archiving and communication server 200, a modality device 300 and an HIS/RIS 400 via an electronic network. The communication controlling device 10 includes various communication protocols for different forms of networks. The electronic network referred to herein means an entire information communication network based on a telecommunication technique, and examples of the electronic network include a hospital backbone LAN, a wireless/wired LAN and the Internet as well as a telephone network, an optical fiber communication network, a cable communication network and a satellite communication network. The medical image processing apparatus 100 obtains inspection data from the picture archiving and communication server 200 or the modality device 300 via the electronic network.

The picture archiving and communication server 200, the HIS/RIS 400 and the medical image processing apparatus 100 may be configured as a cloud medical image processing system. In such a case, the medical image processing apparatus 100 of the medical image processing system can obtain a medical image from the picture archiving and communication server 200 or the modality device 300, for example, via a network.

Examples of the modality device 300 include various kinds of medical imaging devices such as an X-ray computed tomography (CT) device, a magnetic resonance imaging (MRI) device, a positron emission tomography (PET) device and an ultrasonic diagnostic device. Data to be input to the medical image processing apparatus 100 is volume data formed by a plurality of slice images.

The medical image processing apparatus 100 is connected to the HIS/RIS 400. The HIS/RIS 400 is a system that processes an inspection request or the like made by a doctor or the like, which is referred to as an inspection order. The medical image processing apparatus 100 can obtain, via the electronic network, patient information including a patient ID that uniquely identifies a patient or the name, sex, build of a patient and study information including the type of the study, the object of the study or the type of the modality device.

The main control unit 30 executes a program stored in the storage unit 20 to detect the position (anatomical position) of a local structure in a medical image, generate an imaging range image, or generate a mapping chart that associates the position of a local structure in a human body chart such as an anatomical chart with the anatomical position detected from the medical image, for example. In the following description, the position in a patient coordinate system of a local structure detected in a medical image will be referred to as an anatomical position as required.

The storage unit 20 is formed by a storage medium such as a RAM or a ROM and comprises a storage medium that can be read by the main control unit 30, such as a magnetic storage medium, an optical storage medium or a semiconductor memory. Some or all of the programs and data in the storage medium may be downloaded via the electronic network. The medical image processing apparatus 100 may identify the anatomical position based on a program or data stored in advance in the storage unit 20, on data or the like stored in an external storage device accessed via the communication controlling device 10 or on a program stored in an external storage device or the like.

The display unit 40 is formed by a common display device such as a liquid crystal display or an organic light emitting diode (OLED) display and displays an image under the control of the main control unit 30.

The input unit 50 is formed by a common input device such as a keyboard, a touch panel, a ten key or a mouse. The input unit 50 outputs an input signal responsive to selection of a medical image or annotation by a user to the main control unit 30.

Figure 2:
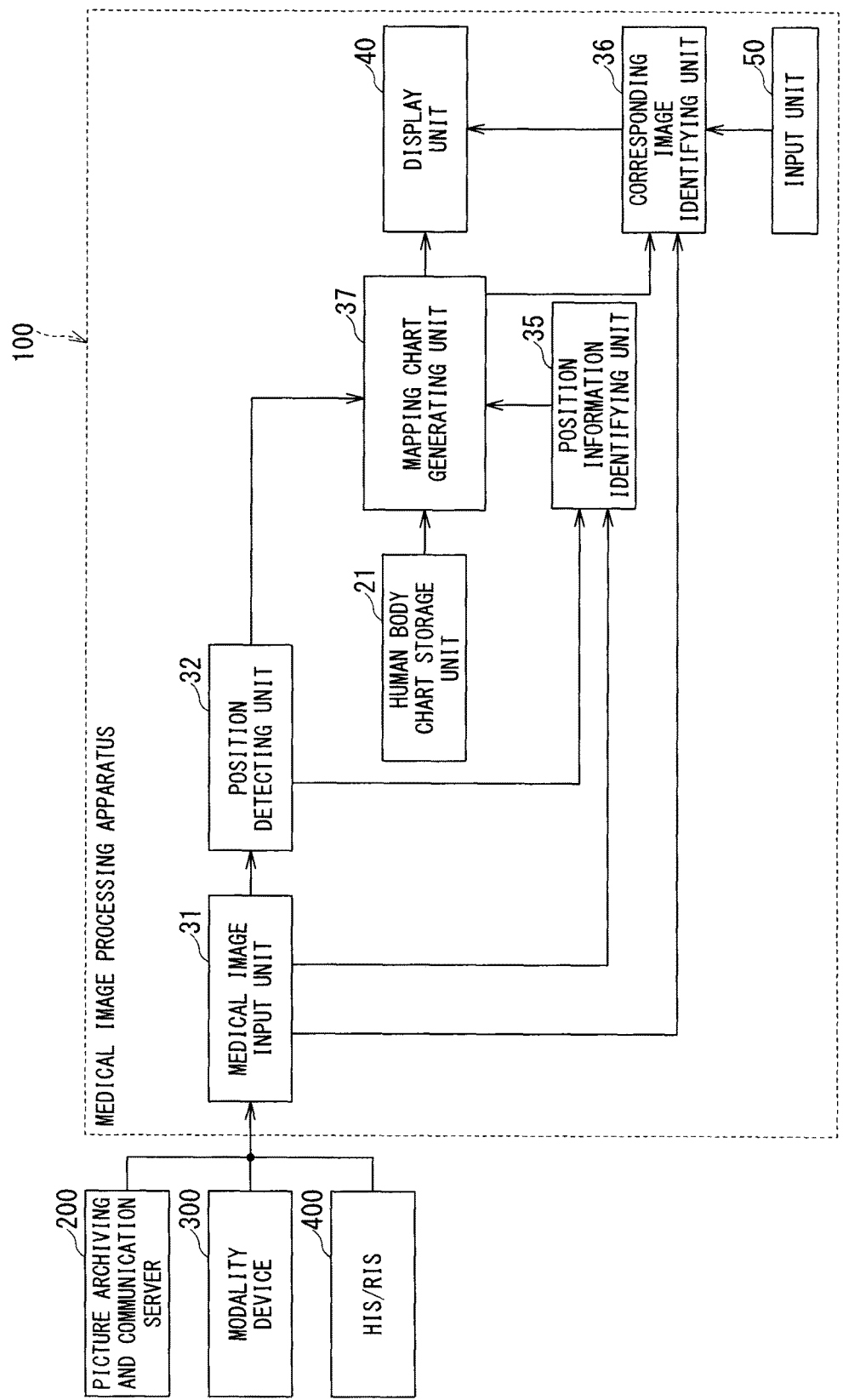
FIG. 2 is a functional block diagram showing an example of a functional configuration of the medical image processing apparatus according to this embodiment.

FIG. 2 is a functional block diagram showing an example of a functional configuration of the medical image processing apparatus 100 according to this embodiment. As shown in FIG. 2, the medical image processing apparatus 100 has a human body chart storage unit 21, a medical image input unit 31, a position detecting unit 32, a position information identifying unit 35, a corresponding image identifying unit 36, a mapping chart generating unit 37, the display unit 40 and the input unit 50. Of these components, the functions of the medical image input unit 31, the position detecting unit 32, the position information identifying unit 35, the corresponding image identifying unit 36 and the mapping chart generating unit 37 are implemented by a processor of the main control unit 30 executing a program stored in the storage unit 20, for example. These functions may be implemented by a plurality of processors cooperating with each other or by a hardware logic without using a CPU. The display unit 40 has a function that is implemented by the main control unit 30 executing a program stored in the storage unit 20 and a display function.

The human body chart storage unit 21 stores a diagram that illustrates the human body (human body chart). The human body chart may be a common human body anatomical chart, for example. The following description will be made in the context of using the human body anatomical chart as the human body chart, as an example. The human body anatomical chart is a diagram that represents viscera, sites and organs in the human body by illustrations or pictures to help understanding of the positions, appearances and shapes of structures in the human body. The anatomical chart may be two-dimensional or three-dimensional. The anatomical chart may be prepared for each site, such as the head or the chest, or for each system, such as the heart, the liver, the respiratory system or the digestive system. The anatomical chart may be prepared for any of the coronal plane, the sagittal plane and the transverse plane. For example, a coronary anatomical chart of a human body may be one of a series of two-dimensional anatomical charts taken from the dorsal side to the ventral side or may be an anatomical chart displayed as a predetermined cross section of a three-dimensional anatomical chart. The anatomical chart may be downloaded from an external storage device, or may be referred to in the external storage device. On the anatomical chart stored in the human body chart storage unit 21, a coordinate system that is associated with local structures, such as viscera, sites and organs, shown in the anatomical chart is previously defined.

Medical image data from the picture archiving and communication server 200 or the modality device 300, for example, is input to the medical image input unit 31. The medical image data may be previously stored in the storage unit 20 via a portable storage medium or a network. A plurality of medical images, each of which is composed of a plurality of sub-images, are input to the medical image input unit 31.

Each of the plurality of medical images may be a bundle of a plurality of sub-images (slice images, for example) forming the medical image. For example, volume data produced based on a plurality of sub-images (slice images, for example) forming the medical image may be input to the medical image input unit 31. The volume data and the plurality of sub-images from which the volume data is produced associated with each other may be input to the medical image input unit 31 as one piece of medical image data. In the following description, the term "medical image data" and "medical image" are interchangeable with the term "volume data" in the context of inputting the volume data to the medical image input unit 31. In the context of selecting and extracting one or more of the plurality of sub-images forming a medical image, the one or more sub-images may be multi planar reconstruction (MPR) images produced based on the volume data.

The position detecting unit 32 detects the anatomical position for the obtained medical image data (the position of the local structure) and adds information on the detected anatomical position (referred to as anatomical position information hereinafter) to the obtained medical image data. The anatomical position information may be previously added to the obtained medical image data. For example, the addition of the anatomical position information to the medical image data may occur when the modality device 300 obtains an image or when an image is stored in the picture archiving and communication server 200. In that case, the detection of the anatomical position and the addition of the anatomical position information to the medical image data by the position detecting unit 32 can be omitted. A method in which the position detecting unit 32 detects the anatomical position will be described later.

The anatomical position information added to the medical image data may be retained in a data format, such as XML data or binary data, and associated with the corresponding medical image data. The input medical image data complies with the digital imaging and communication in medicine (DICOM) format, and the anatomical position information may be retained as supplementary information in the DICOM standard.

The mapping chart generating unit 37 generates a mapping chart. Specifically, the mapping chart generating unit 37 generates a mapping chart by adding at least one of a mark that represents the position of the local structure detected in the medical image and a mark that represents the position of a site of interest on the medical image to the human body chart. The site of interest on the medical image may be an annotation added to the medical image or a site associated with the result of analysis of the medical image. The site associated with the result of analysis of the medical image may be a segmented and labelled region of a particular viscus or lesion, a site that is a target of distance measurement or a site that is a target of angle measurement.

The mapping chart generating unit 37 identifies an imaging range of the medical image based on the anatomical position detected from the medical image data. The imaging range may be indicated by a physical data amount that represents the amount of data contained in the medical image data, such as the number of slices, or indicated in a relative manner based on the distribution of anatomical positions included in the medical image data. The mapping chart generating unit 37 identifies the imaging range of the medical image data based on the distribution of anatomical positions included in the medical image data.

Furthermore, the mapping chart generating unit 37 may generate an imaging range image, such as a rectangular frame that indicates the imaging range, from the identified imaging range. In that case, the mapping chart generating unit 37 may generate the mapping chart by superimposing the imaging range image on the human body chart. In that case, the mapping chart generating unit 37 can generate the mapping chart by adding at least one of the mark that represents the position of the local structure detected in the medical image and the mark that represents the position of an annotation attached to the medical image to the human body chart and then superimposing the imaging range on the human body chart. Alternatively, the mapping chart generating unit 37 may generate a mapping chart using a medical image (photograph) instead of the human body chart. A method in which the mapping chart generating unit 37 generates a mapping chart will be described later.

The mapping chart generating unit 37 makes the display unit 40 display the generated mapping chart.

The position information identifying unit 35 calculates position information on the annotation based on the anatomical position detected from the medical image. The position information identifying unit 35 identifies a coordinate on the human body chart for the annotation, which is the site of interest in the medical position. In addition, the position information identifying unit 35 calculates the position information on the annotation based on the anatomical position. The "position information" refers to the distance or direction from the anatomical position to the annotation. The position information is not exclusively the position information on the annotation, and position information on a coordinate on the medical image selected by an input from the input unit 50 provided with a mouse or the like can be calculated in the same way. The processing of the position information identifying unit 35 will be described later.

Based on the coordinate of the annotation on the human body chart identified by the position information identifying unit 35, the mapping chart generating unit 37 can generate the mapping chart that is the human body chart with the mark representing the position of the annotation attached thereto.

That is, the mapping chart generating unit 37 generates a mapping chart by adding at least one of the mark that represents the position of the local structure detected in the medical image and the mark that represents the position of the annotation attached to the medical image to the human body chart. Furthermore, the mapping chart generating unit 37 may generate a mapping chart by superimposing the imaging range image on the human body chart. Furthermore, the mapping chart generating unit 37 may generate a mapping chart by adding at least one of the mark that represents the position of the local structure detected in the medical image and the mark that represents the position of the annotation attached to the medical image to the human body chart and then superimposing the imaging range on the human body chart.

The position information identifying unit 35 may obtain information on the result of analysis of the medical image by using an analysis function of the medical image processing apparatus 100 or obtain the information from the picture archiving and communication server 200 or the modality device 300 via a network. In that case, the position information identifying unit 35 identifies a coordinate on the medical image and a coordinate on the human body chart for a site associated with the result of analysis.

In this process, the mapping chart generating unit 37 can superimpose a mark that represents the position of the site associated with the result of analysis of the medical image on the mapping chart. Alternatively, the mapping chart generating unit 37 may superimpose an image that represents the result of analysis (including a comment about the result of analysis) on the mapping chart. In that case, the user can easily grasp the result of analysis of the medical image by checking the mapping chart.

The information on the result of analysis obtained by the position information identifying unit 35 may be information on a segmented and labelled region of a particular viscus or lesion, for example. Since a region is formed by a collection of points, the position information identifying unit 35 can identify the region associated with the result of analysis on the human body chart in a coordinate transformation method similar to the annotation. In this process, the mapping chart generating unit 37 can generate a mapping chart on which an image that emphasizes the region associated with the result of analysis (including an image that emphasizes the contour of the region) is superimposed as a mark that indicates the position of the site associated with the result of analysis of the medical image.

The information on the result of analysis obtained by the position information identifying unit 35 may be information on the result of measurement calculated based on the medical image. Such a result of measurement may be the result of measurement of a straight distance between two points, the result of measurement of a curve distance along a particular structure such as a blood vessel, or the result of measurement of an angle between two straight lines, for example.

In the case of the result of measurement of a straight distance, for example, an image of a straight line corresponding to the measured straight distance and an image indicating end points of the straight line can be superimposed on the mapping chart as marks that indicate a position that corresponds to the result of analysis of the medical image by coordinate transformation of the end points of the straight line. In the case of the result of measurement of a curve distance, an image of a curve corresponding to the measured curve distance can be superimposed on the mapping chart as a mark that indicates a position that corresponds to the result of analysis of the medical image by coordinate transformation of a point forming the curve. In the case of the result of measurement of an angle, an image of three points and two straight lines corresponding to the measured angle can be superimposed on the mapping chart as marks that indicate a position that corresponds to the result of analysis of the medical image by coordinate transformation of the three points that define the measured angle.

In the following description, the mapping chart that is the human body chart with the mark that indicates the position of a local structure will be referred to as a mapping anatomical chart, as required. Of the mapping anatomical charts, a mapping anatomical chart including an imaging range image will be referred to as an anatomical chart with an imaging range image, as required. Of the anatomical charts with an imaging range image, an anatomical chart with a mark that indicates the position of an annotation will be referred to as an anatomical chart with an annotation, as required. As described above, an image that represents a mark that indicates the position of a site associated with the result of analysis of a medical image or the result of analysis may be superimposed on the mapping chart.

The display unit 40 displays the mapping chart (such as a mapping anatomical chart, an anatomical chart with an imaging range image, or an anatomical chart with an annotation). Based on the position information on the annotation calculated by the position information identifying unit 35, the mapping chart generating unit 37 generates an image, such as a character string, that represents the position information and makes the display unit 40 display the image.

The corresponding image identifying unit 36 identifies a slice image that corresponds to the annotation or anatomical position selected on the mapping chart, such as the mapping chart, the anatomical chart with an imaging range image or the anatomical chart with an annotation, from among medical images. The corresponding image identifying unit 36 makes the display unit 40 display the identified slice image. A method in which the corresponding image identifying unit 36 identifies a slice image will be described later.

(2) Operation

First Embodiment

Figure 3:
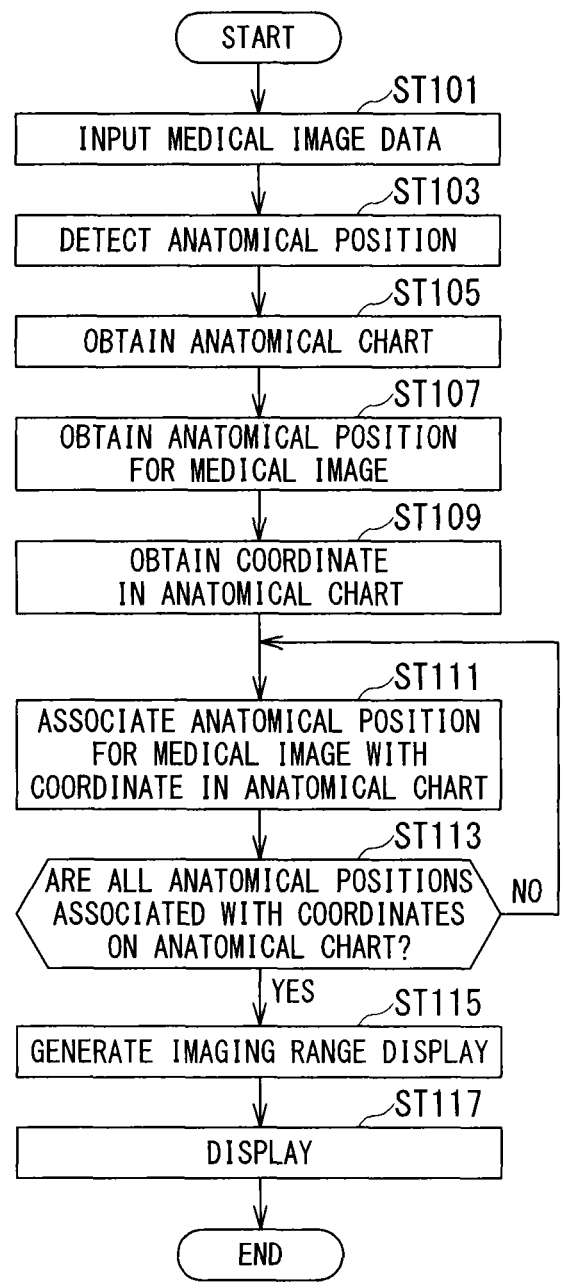
FIG. 3 is a flowchart showing an example of an operation of the medical image processing apparatus according to a first embodiment.

FIG. 3 is a flowchart showing an example of an operation of the medical image processing apparatus 100 according to a first embodiment. FIG. 3 shows an example of a procedure of generating an anatomical chart with an imaging range image.

In ST101, medical image data composed of a plurality of images is input to the medical image input unit 31 from the picture archiving and communication server 200 or the modality device 300. For example, the medical image data is volume data produced based on a plurality of sub-images (slice images, for example) forming a medical image corresponding to the medical image data. Alternatively, the volume data and the plurality of sub-images from which the volume data is produced associated with each other may be input to the medical image input unit 31 as one piece of medical image data.

In ST103, the position detecting unit 32 detects an anatomical position for the input medical image data.

Figure 4A:
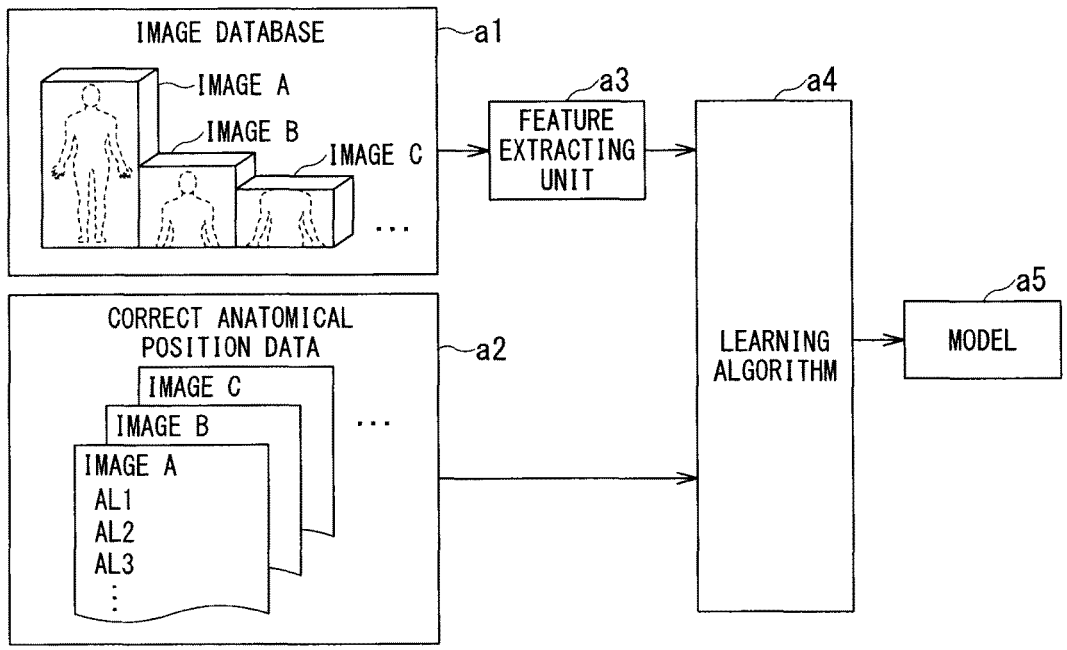
FIG. 4A shows an example of a method of producing a model a5 used for detecting an anatomical position.

FIG. 4 are diagrams for illustrating a method of detecting an anatomical position. FIG. 4A shows an example of a method of producing a model a5 used for detecting an anatomical position. The model a5 shown in FIG. 4A may be previously stored in the storage unit 20 of the medical image processing apparatus 100 or in an external storage device.

As shown in FIG. 4A, the model 5a used for detecting an anatomical position is produced by common machine learning or pattern recognition. FIG. 4A shows an example in which the model a5 is produced using an image database a1 and correct anatomical position data a2. The image database a1 is a collection of volume data obtained by an X-ray CT apparatus or an MRI apparatus for various objects of different body shapes. As illustrated in FIG. 4A, the image database a1 includes not only the volume data on a whole body (image A) but also volume data of an image of a part of a body (images B and C). The correct anatomical position data a2 is data on a correct anatomical position previously determined by an expert such as a doctor for each image in the image database a1. As shown in FIG. 4A, a feature extracting unit a3 extracts a feature from each piece of volume data in the image database a1, and a learning algorithm a4 produces the model a5 using the correct anatomical position data a2. The model a5 is used to associate the feature extracted from the image database a1 with an anatomical position. The model a5 is a model based on machine learning, for example. Different models a5 may be produced for different sexes, ages, races or builds, or a single model a5 that accommodates for such differences may be produced.

Figure 4B:
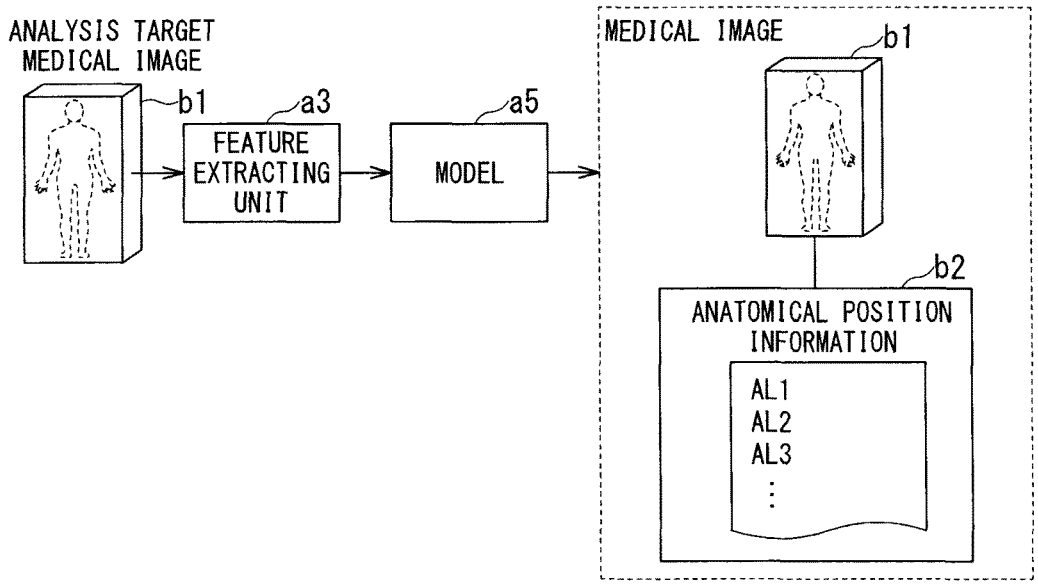
FIG. 4B shows an example of a process performed by the position detecting unit.

FIG. 4B shows an example of a process performed by the position detecting unit 32. As with the feature extracting unit a3 shown in FIG. 4A, the position detecting unit 32 extracts a feature from analysis target image data b1 for which the anatomical position is unknown, and detects the anatomical position using the model a5 already produced. More specifically, the position detecting unit 32 detects a local structure in the medical image and calculates the position of the detected local structure in the medical image as the anatomical position. Anatomical position information b2 thus calculated is added to the analysis target image data b1.

The anatomical position described above is not exclusively detected in the process described above and can also be detected with a mathematical statistic framework referred to as computational anatomy (computational anatomical model).

FIG. 5 are diagrams for illustrating kinds of local structures. A local structure is a characteristic structure in the human body that is important for understanding a medical image and is sometimes referred to as an anatomical landmark (AL). For example, FIG. 5A shows examples of local structures of a head and a neck. From the top to the bottom of the list, FIG. 5A shows an anterior arch (tubercle) of atlas (cervical vertebra I), a superior tip of dens/peg (cervical vertebra II), a superior aspect of right eye globe, a superior aspect of left eye globe, a center of a right eye globe and a center of a left eye globe. Similarly, FIG. 5B shows, as local structures of a chest, a bifurcation of trachea, an apex of a right lung, an apex of a left lung, an inferior angle of a right scapula, an inferior angle of a left scapula and a start of left subclavian artery (branching off aortic arch). FIG. 5C shows, as local structures of an abdomen, a superior pole of a right kidney, a superior pole of a left kidney, an inferior pole of a right kidney, an inferior pole of a left kidney, a head of a pancreas and a tip of a tail of a pancreas. FIG. 5D shows, as local structures of lower limbs, a lateral epicondyle of a right femur, a medial epicondyle of a right femur, a lateral epicondyle of a left femur, a medial epicondyle of a left femur, a lateral condyle of a right tibia and a medial condyle of a right tibia. Local structures of a whole body are defined with the grading shown in FIG. 5, for example and a plurality of local structures are defined for each of various bones, muscles, viscus or the like of the human body. The anatomical position is detected for each of these local structures.

The anatomical position is retained in a state where the anatomical position is associated with the medical image data as the anatomical position information. For example, the anatomical position information may be retained as a database in the storage unit 20 or the like in an XML or text format, for example, in a state where the anatomical position information is associated with an ID or the like that uniquely identifies the medical image. Alternatively, the anatomical position information may be retained in a state where the anatomical position information is integrated with the medical image data as supplementary information in DICOM.

The anatomical position information can include not only the information on the anatomical position but also site information on the chest, the abdomen or the like to which the local structure corresponding to the anatomical position belongs and body tissue information on a functional system in the human body, such as a skeletal system or a respiratory system, to which the local structure corresponding to the anatomical position belongs, for example.

Figures 6A, 6B:
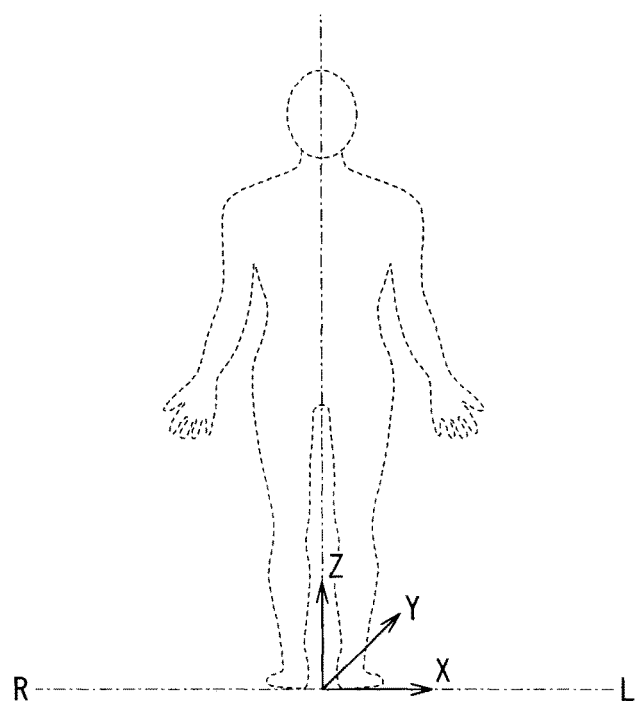
FIG. 6A shows an example of the anatomical position information.
FIG. 6B is a diagram for illustrating a patient coordinate system.

FIG. 6 are diagrams for illustrating the anatomical position information. The table of FIG. 6A shows an example of the anatomical position information. From the left to the right, as the anatomical position information, the table of FIG. 6A shows an identifier, a name, a reliability, a site, a body tissue, positions in a patient coordinate system (X-axis, Y-axis and Z-axis) of an anatomical position. FIG. 6A shows part of the anatomical position information on the abdomen, as an example. From the left to the right, the first row of the table of FIG. 6A shows an identifier (ABDO25. C), a name (center of body of L5), a reliability (0.87), a site (abdomen), a body tissue (skeletal system), positions in a patient coordinate system (X-axis (−3.1), Y-axis (23.4), Z-axis (90.0)). Similarly, a second row of the table shows an identifier (ABDO32. C), a name (superior aspect of right iliac spine), a reliability (0.82), a site (abdomen), a body tissue (skeletal system), positions in a patient coordinate system (X-axis (−11.1), Y-axis (−54.4), Z-axis (84.1)), and a third row of the table shows an identifier (ABDO39. C), a name (superior aspect of left iliac spine), a reliability (0.83), a site (abdomen), a body tissue (skeletal system), positions in a patient coordinate system (X-axis (−3.0), Y-axis (30.0), Z-axis (104.0)).

The identifier is an ID that uniquely identifies the anatomical position. The name is a name of the local structure and is represented by a technical term of anatomy or medicine. The reliability is a numerical value that indicates the precision of the anatomical position. Since the anatomical position is data computationally estimated by a machine learning algorithm or pattern recognition, the numerical value that indicates the precision of the computation of the position is used. In the example shown in FIG. 6A, the numerical value ranges from 0 to 1, and the closer to 1, the higher the reliability is. The site refers to a site of the human body to which the local structure belongs and means a sort such as chest or abdomen. The body tissue is sorted based on the function of the local structure and is represented by the nerve system, the skeletal system or the respiratory system, for example. Furthermore, a viscus name, such as heart, lung or femur, or information on an anatomical structural unit other than the site or the body tissue may be provided as the anatomical position information. The positions in the patient coordinate system are X-axis, Y-axis and Z-axis coordinates that indicate the anatomical position.

FIG. 6B is a diagram for illustrating a patient coordinate system. As shown in FIG. 6B, the patient coordinate system is a coordinate system whose X-axis extends in a left-right direction of the patient, whose Y-axis extends in a dorsal-ventral direction of the patient, and whose Z-axis extends in a head-foot direction of the patient. The X coordinate increases as it goes from the center of the body of the patient to the right, the Y coordinate increases as it goes from the center of the body of the patient to the dorsal side, and the Z coordinate increases as it goes from the foot to the head of the patient. The positions in the patient coordinate system are relatively expressed with respect to an arbitrary position, such as a reference position included in the volume data.

Note that FIG. 6 show just an example of the anatomical position information and the data format thereof.

Description with reference to FIG. 3 will be resumed.

In ST105, the mapping chart generating unit 37 obtains an anatomical chart from the human body chart storage unit 21.

In ST107, the mapping chart generating unit 37 obtains the detected anatomical position for the input medical image.

In ST109, the mapping chart generating unit 37 obtains a coordinate on the anatomical chart that corresponds to the detected anatomical position for the medical image.

In ST111, the mapping chart generating unit 37 generates a mapping chart (mapping anatomical chart) by associating the detected anatomical position (position of the local structure) for the input medical image with the coordinate on the anatomical chart corresponding to the local structure and imparting a mark that represents the anatomical position (position of the local structure) for the medical image data to the coordinate of the local structure in the anatomical chart.

In ST113, the mapping chart generating unit 37 determines whether or not a mark has been imparted to the coordinate on the anatomical chart for every anatomical position included in the medical image data. If the association has been completed for all the anatomical positions, the processing of ST115 is performed. If the association has not been completed, the processing of ST111 is repeated.

In ST115, the mapping chart generating unit 37 detects an imaging range for the medical image based on the distribution of the anatomical positions on the mapping chart and generates an imaging range image that indicates the imaging range.

In ST117, the mapping chart generating unit 37 generates an anatomical chart with an imaging range image, which is the mapping chart (mapping anatomical chart) on which the imaging range image is superimposed, and makes the display unit 40 display the anatomical chart with the imaging range image.

Figures 7A, 7B:
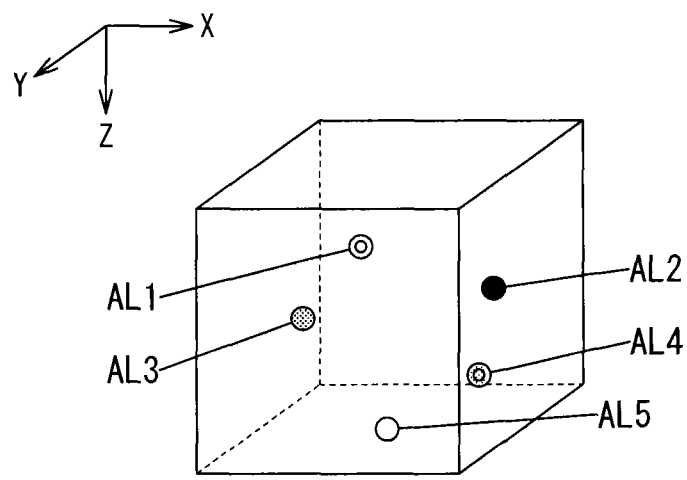
FIG. 7A shows an example of the medical image data input to the medical image processing apparatus.
FIG. 7B shows the anatomical positions as voxel coordinates for the medical image data.

FIG. 7 are diagrams for illustrating a coordinate of an anatomical position included in a medical image for the medical image processing apparatus 100 according to the first embodiment. FIG. 7A shows an example of the medical image data input to the medical image processing apparatus 100. Each circle included in the medical image data shown in FIG. 7A represents an anatomical position. A double circle represents an anatomical position "AL1", a black circle represents an anatomical position "AL2", a hatched circle represents an anatomical position "AL3", a hatched double circle represents an anatomical position "AL4", and a white circle represents an anatomical position "AL5". The five anatomical positions detected in the medical image shown in FIG. 7A are retained as the anatomical position information and associated with the medical image. The anatomical position information includes coordinate information that indicates the anatomical positions, which is referred to as a patient coordinate system. When the anatomical position information for the medical image data is generated, the anatomical position information may be retained in a voxel coordinate system for the medical image data, rather than in the patient coordinate system. The voxel coordinate system is a three-dimensional orthogonal coordinate system that represents a voxel position for volume data. A coordinate of a voxel close to the anatomical position identified for medical image data may be used as coordinate information that indicates the anatomical position. Voxel coordinates shown in FIG. 7A are X, Y and Z coordinates with respect to an upper left corner of the volume data as an origin.

In FIG. 7B, the anatomical positions are shown as voxel coordinates for the medical image data. In the example shown in FIG. 7B, voxel coordinates for the anatomical positions shown in FIG. 7A are shown. In the example shown in FIG. 7B, the voxel coordinates of the anatomical position "AL1" are (Xa1, Ya1, Za1). Similarly, the voxel coordinates of the anatomical position "AL2" are (Xa2, Ya2, Za2), the voxel coordinates of the anatomical position "AL3" are (Xa3, Ya3, Za3), the voxel coordinates of the anatomical position "AL4" are (Xa4, Ya4, Za4), and the voxel coordinates of the anatomical position "AL5" are (Xa5, Ya5, Za5).

As shown in the example in FIG. 7, the mapping chart generating unit 37 can obtain the coordinates of the anatomical position for the input medical image as voxel coordinates or other coordinates (ST107). The medical image data includes information on an imaging condition as supplementary information. The imaging condition may be a pixel size, a slice thickness, a slice interval, an imaging starting point or a reference position, for example. As shown in FIG. 7A, supposing that the medical image data is sliced along the Z-axis, an anatomical position represented in the patient coordinate system can be converted into X and Y coordinates and a slice number of a slice image in the medical image data.

The mapping chart generating unit 37 further obtains a coordinate on the anatomical chart that corresponds to the anatomical position for the input medical image (ST109).

Figures 8A, 8B:
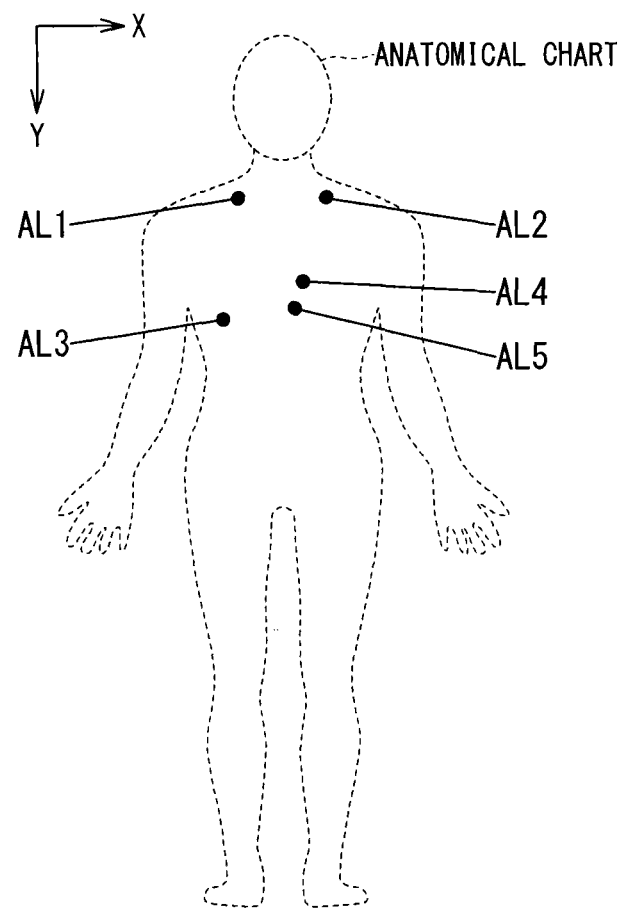
FIG. 8A shows an example of a two-dimensional anatomical chart.
FIG. 8B is a table showing coordinates on the anatomical chart that corresponds to the five anatomical positions included in the input medical image data.

FIG. 8 are diagrams for illustrating coordinates in an anatomical chart that correspond to anatomical positions included in the medical image for the medical image processing apparatus 100 according to the first embodiment. FIG. 8A shows an example of a two-dimensional anatomical chart. Although FIG. 8A shows an anatomical chart showing only the contour of the human body, the anatomical chart may further show a structure, such as a viscus or a bone, or an internal structure thereof inside the contour of the human body. In the anatomical chart, positions of local structures that correspond to all the anatomical positions detected by the position detecting unit 32 are defined.

In the example shown in FIG. 8A, positions of the local structures on the anatomical chart that correspond to the five anatomical positions included in the input medical image data shown in FIG. 7 are shown. For example, the anatomical position "AL1" in the medical image data shown in FIG. 7A corresponds to the position of "AL1" in the anatomical chart shown in FIG. 8A. The position of "AL1" on the anatomical chart shown in FIG. 8A corresponds to a coordinate on the anatomical chart of the local structure that corresponds to the anatomical position "AL1".

FIG. 8B is a table showing coordinates on the anatomical chart that correspond to the five anatomical positions included in the input medical image data. Positions on the anatomical chart that correspond to the five anatomical positions "AL1", "AL2", "AL3", "AL4" and "AL5" shown in the table of FIG. 7B are shown by X and Y coordinates. The Z-axis that represents the head-foot direction in the medical image data corresponds to the Y-axis in the anatomical chart. In the example of FIG. 8B, the anatomical chart coordinates of the anatomical position "AL1" are (Xb1, Yb1). Similarly, the anatomical chart coordinates of the anatomical position "AL2" are (Xb2, Yb2), the anatomical chart coordinates of the anatomical position "AL3" are (Xb3, Yb3), the anatomical chart coordinates of the anatomical position "AL4" are (Xb4, Yb4), and the anatomical chart coordinates of the anatomical position "AL5" are (Xb5, Yb5).

The mapping chart generating unit 37 associates the coordinates of the anatomical positions for the input medical image described with reference to FIG. 7 with the coordinates on the anatomical chart that correspond to the coordinates of the anatomical positions for the medical image described with reference to FIG. 8 (ST111). For example, the coordinates on the anatomical chart that correspond to the anatomical position "AL1" (X1a, Y1a, Z1a) shown in FIG. 7B are the coordinates (Xb1, Yb1) of the anatomical position "AL1" shown in a first row in FIG. 8B.

The mapping chart generating unit 37 performs such association for all the anatomical positions detected for the medical image data to generate a mapping chart (ST113).

Figure 9:
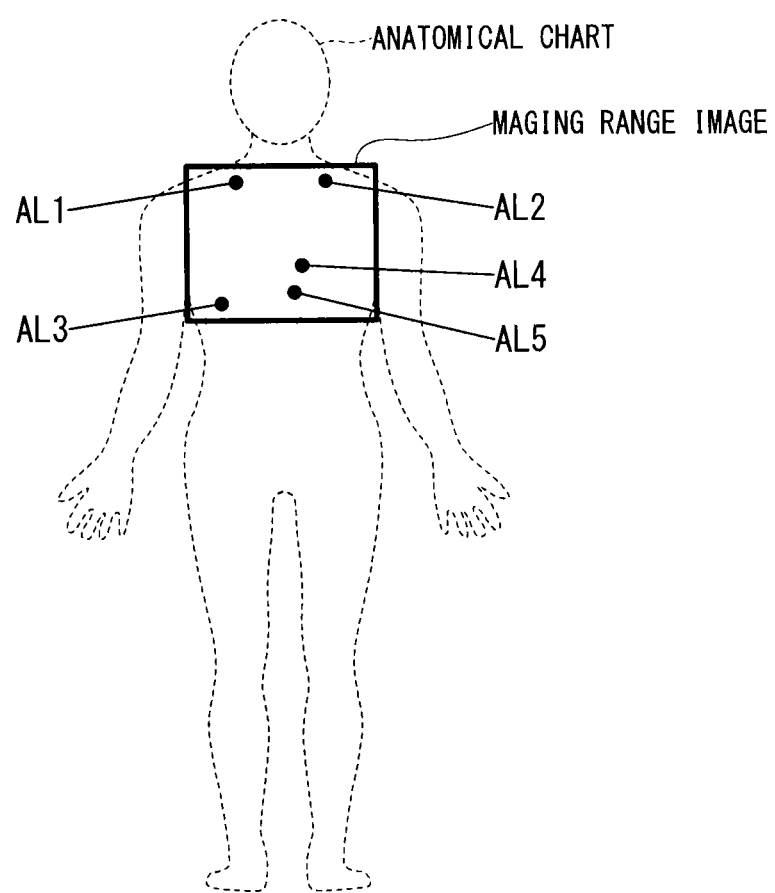
FIG. 9 is a diagram for illustrating an imaging range image for the medical image processing apparatus according to the first embodiment.

FIG. 9 is a diagram for illustrating an imaging range image for the medical image processing apparatus 100 according to the first embodiment. The imaging range image is a mapping chart that shows the imaging range for the input medical image data based on the anatomical positions included in the medical image data.

FIG. 9 shows an example of the anatomical chart with an imaging range image, which is the mapping chart on which the imaging range image is superimposed. If the five anatomical positions "AL1", "AL2", "AL3", "AL4" and "AL5" are anatomical positions identified based on the medical image, the mapping chart generating unit 37 generates the imaging range image so as to enclose these anatomical positions (ST115).

FIG. 9 shows an example in which a rectangular frame enclosing the five anatomical positions as the imaging range image. The imaging range image may be such a rectangular frame or may be defined by choosing an anatomical position whose coordinate in a predetermined direction (Y coordinate as a body axis direction, for example) is the smallest as an end of the imaging range image in the predetermined direction and an anatomical position whose coordinate in the predetermined direction is the greatest as an opposite end of the imaging range image in the predetermined direction. In the latter case, the imaging range image may be a boundary line that has an upper end at the anatomical position having the smallest Y coordinate and a lower end at the anatomical position having the greatest Y coordinate. The imaging range image may have a certain margin so as to enclose the anatomical positions. Furthermore, points that indicate the anatomical positions that indicate the upper end and lower end of the imaging range image, or the imaging range image itself defined by a rectangular frame or a boundary line may be highlighted in a different color. Furthermore, information that indicates a local structure included in the imaging range may be additionally displayed on the anatomical chart. The information that indicates a local structure may be a contour line or a symbol, such as a schema diagram, of an anatomical site of a viscus or the like that corresponds to the local structure.

The medical image data includes information on the number of images, the imaging start position or the imaging end position as supplementary information. The mapping chart generating unit 37 may generate the imaging range image by taking into consideration not only the distribution of the anatomical positions but also the number of images, the imaging start position or the imaging end position. For example, the imaging range may be calculated from the position of the slice including the local structure that correspond to the anatomical positions and the total number of images, or may be determined by identifying the anatomical positions that correspond to the imaging start position and the imaging end position. Alternatively, the imaging range may be displayed based on various types of information concerning a study or the patient included in the supplementary information to the medical image. Alternatively, a viscus or site to be inspected may be determined from study information obtained from the HIS/RIS 400, and an imaging range that corresponds to the site may be displayed.

Although FIG. 9 shows an example in which points that indicate the anatomical positions and a local structure that corresponds to the anatomical positions are displayed on the anatomical chart with an imaging range image, such a display may be omitted or may be provided by mouse over or by placing a pointer or cursor thereon.

The anatomical chart with an imaging range image generated as described above is displayed by the display unit 40 (ST117). In the following, various display examples of the anatomical chart with an imaging range image will be described with reference to FIGS. 10 to 13. The medical image processing apparatus 100 according to this embodiment can select a medical image for radiological interpretation, provide a guide to the position where the medical image under radiological interpretation is displayed, or control movement to a slice image that corresponds to the anatomical position selected in the medical image.

Figure 10A:
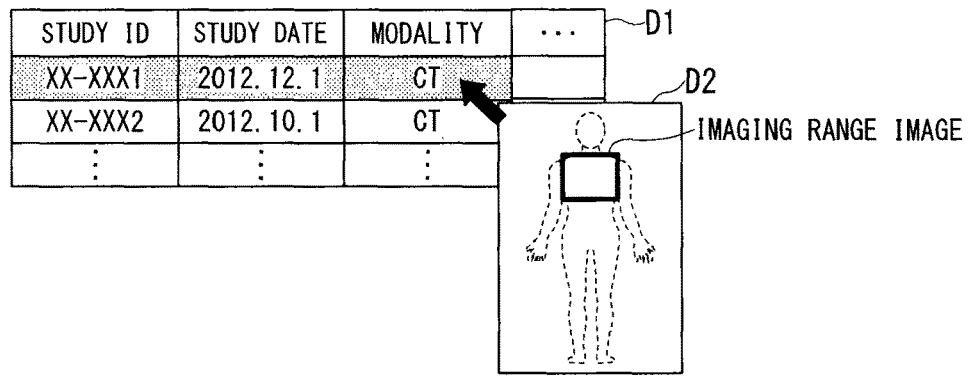
FIG. 10A shows a medical image list D1 that displays a list of input medical images in a table format as an example.
Figure 10B:
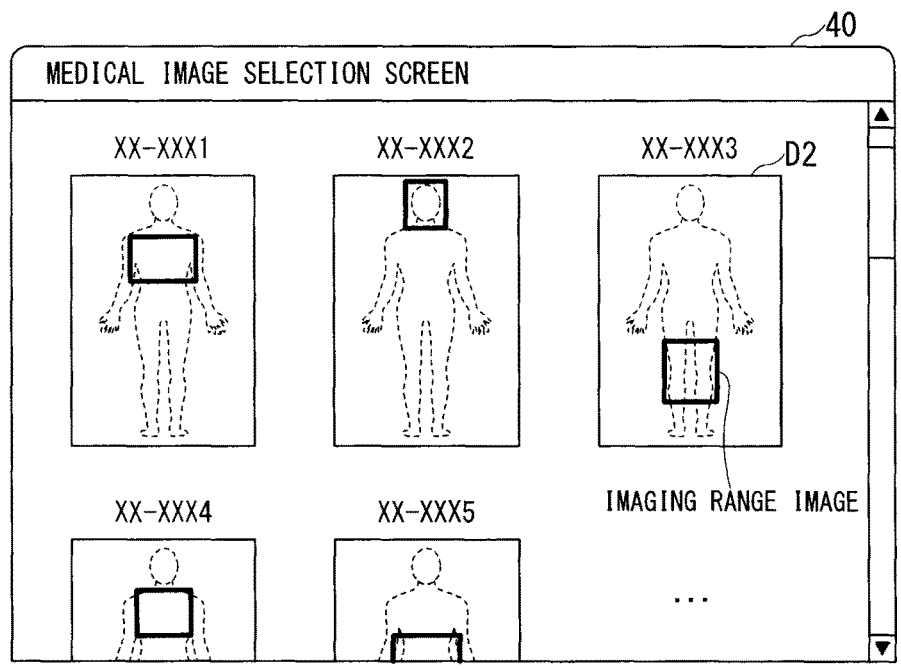
FIG. 10B shows a modification of the display example shown in FIG. 10A.
Figure 10C:
FIG. 10C shows a modification of the display examples shown in FIGS. 10A and 10B.

FIG. 10 are diagrams for illustrating examples of how the imaging range image is displayed when a medical image is selected in the medical image processing apparatus 100 according to the first embodiment. FIGS. 10A, 10B and 10C show examples of how the imaging range image is displayed when one piece of medical image data that is a target of creation of a radiological interpretation report is selected from among a plurality of pieces of input medical image data.

FIG. 10A shows a medical image list D1 that displays a list of input medical images in a table format as an example. FIG. 10A shows an example in which a pointer or cursor is placed on medical image data denoted by a study ID "XX-XXX1" in a first row of the medical image list D1 in response to an input from the input unit 50 provided with a mouse or the like. FIG. 10A shows an example in which an anatomical chart D2 with an imaging range image that corresponds to the row on which the pointer or cursor is placed is popped up in a vicinity of the pointer or cursor.

Since the anatomical chart D2 with an imaging range image is displayed at the same time when the medical image is selected, the imaging range for each medical image data displayed in the medical image list D1 can be visually checked before the medical image data is actually opened. Although FIG. 10A shows an example in which the anatomical chart D2 with an imaging range image is displayed in a vicinity of the pointer or cursor, a region for displaying the anatomical chart D2 with an imaging range image may be previously prepared on a screen.

FIG. 10B shows a modification of the display example shown in FIG. 10A. FIG. 10B shows an example in which the anatomical chart D2 with an imaging range image is displayed as an icon that represents each piece of medical image data, while FIG. 10A shows an example in which the input medical image data is displayed in a table format. Desired medical image data can be opened by using the input unit 5 provided with a mouse or the like to select a corresponding icon from among the icons that represent the medical image data.

FIG. 10C also shows a modification of the display examples shown in FIGS. 10A and 10B. FIG. 10C shows an example in which a partial anatomical chart is displayed as the anatomical chart D2 with an imaging range image that corresponds to the medical image data in the medical image list D1. The partial anatomical chart may be any of various kinds of anatomical charts stored in the human body chart storage unit 21. An anatomical chart may be selected based on information on a site or viscus included in the anatomical position information, and an anatomical chart D2 with an imaging range image that is the selected anatomical chart on which the imaging range image is superimposed may be displayed. Alternatively, a schema diagram that corresponds to a site or viscus to be imaged may be displayed as the anatomical chart D2 with an imaging range image, as shown in the imaging range column in FIG. 10C. Furthermore, the mapping chart generating unit 37 may generate the imaging range image by trimming the anatomical chart based on the imaging range.

In the example shown in FIG. 10C, anatomical charts D2 with an imaging range image that are partial anatomical charts are displayed in a column of the medical image list D1. Since the anatomical charts D2 with an imaging range image are integrated into the medical image list D1, grasp of medical image data and selection of a medical image that is a target of radiological interpretation can be facilitated. Information used to select from these partial anatomical charts may be obtained from supplementary information to the medical image, study information or the like obtained from the HIS/RIS 400 or the like.

Figure 11:
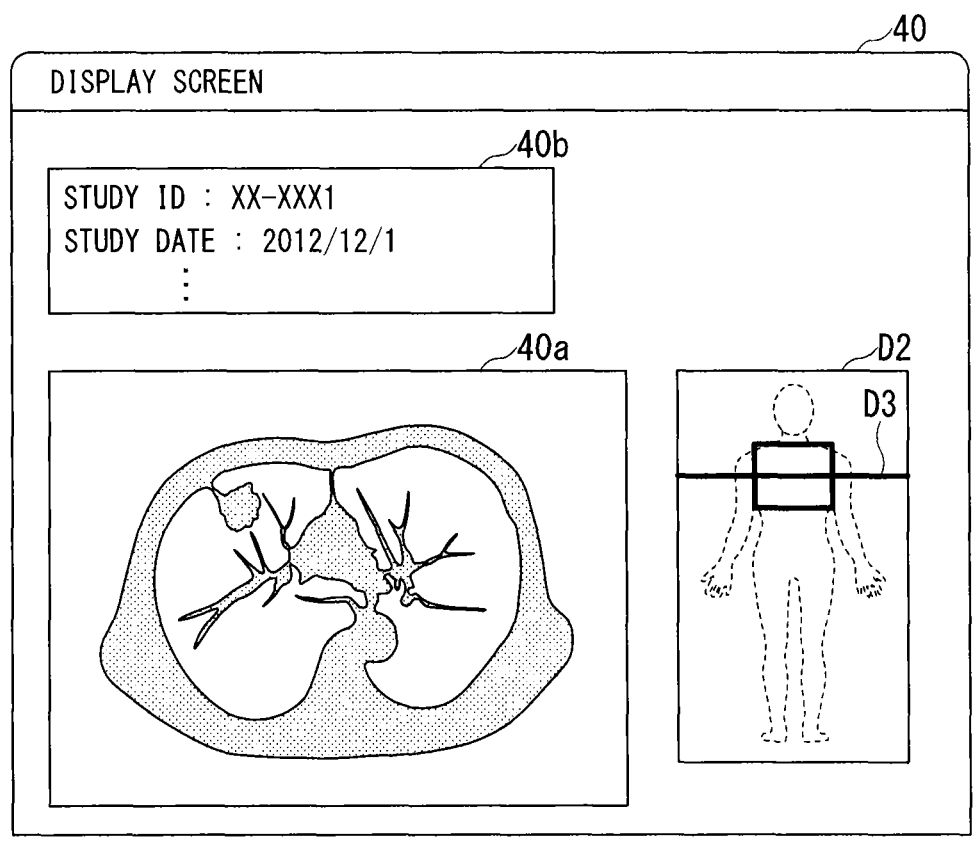
FIG. 11 is a diagram for illustrating a first display example of the imaging range image in a display for a medical image of the medical image processing apparatus according to the first embodiment.

FIG. 11 is a diagram for illustrating a first display example of the imaging range image in a display for a medical image of the medical image processing apparatus 100 according to the first embodiment. FIG. 11 shows an example in which a slice image 40a included in the medical image data that is a target of radiological interpretation is displayed on the display unit 40. In an upper part of the display unit 40 in FIG. 11, a study information display field 40b in which study information or the like in the displayed medical image data is displayed. An example of the slice image 40a included in the medical image data is displayed below the study information display field 40b. The medical image data is volume data composed of a plurality of slice images. Radiological interpretation is performed by displaying one by one the plurality of slice images included in the medical image data and sequentially changing the slice images in response to an input from the input unit 50 provided with a mouse or the like. In the example shown in FIG. 11, the anatomical chart D2 with an imaging range image is displayed at a side of the slice image 40a. An indicator D3 that indicates the position where the slice image is displayed is provided in the anatomical chart D2 with an imaging range image and indicates where the slice image 40a is currently displayed in the imaging range. Furthermore, the slice image 40a may be replaced with a slice image including an anatomical site that corresponds to the position where the indicator D3 is displayed, by moving the indicator D3 shown in FIG. 11 to an upper limit. A coordinate of the anatomical chart D2 with an imaging range image is associated with the anatomical position detected for the medical image data under radiological interpretation. Therefore, a slice image including an anatomical position that corresponds to the coordinate of the anatomical chart D2 with an imaging range image may be displayed by pressing the screen at a desired part of the anatomical chart D2 with an imaging range image. Such identification of the slice image including the anatomical position that corresponds to the coordinate of the anatomical chart D2 with an imaging range image is performed by the corresponding image identifying unit 36. A processing of the corresponding image identifying unit 36 will be described later.

Although FIG. 11 shows an example in which the anatomical chart D2 with an imaging range image is displayed at a right side of the slice image 40a, the anatomical chart D2 with an imaging range image may be displayed in the display region of the slice image 40a. For example, a reduced-size anatomical chart D2 with an imaging range image may be displayed above the slice image 40a on the right side thereof.

FIG. 12 are diagrams for illustrating second display examples of the imaging range image in a display of the medical image in the medical image processing apparatus 100 according to the first embodiment. While FIG. 11 shows an example in which the imaging range image is superimposed on the anatomical chart of the whole body, FIG. 12 show examples of the anatomical chart D2 with an imaging range image produced by trimming the anatomical chart with the imaging range image. FIG. 12 show examples in which an anatomical chart of lungs is trimmed. As in the example shown in FIG. 11, the anatomical chart D2 with an imaging range image shown in FIG. 12 is displayed at a side of the slice image or in the display region of the slice image.

Figure 12A:
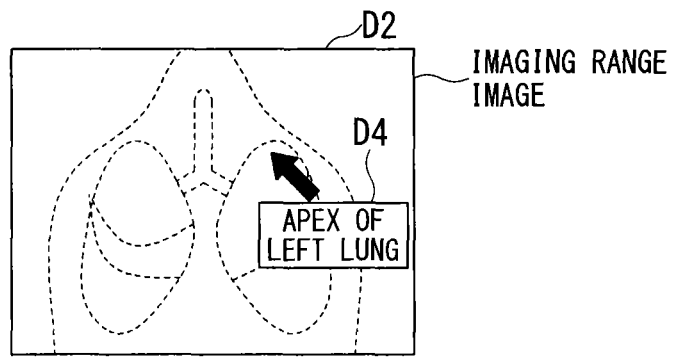
FIG. 12A shows an example in which the pointer or cursor is placed at a coordinate of the anatomical chart D2 with an imaging range image that is associated with the anatomical position for the medical image data.

FIG. 12A shows an example in which the pointer or cursor is placed at a coordinate of the anatomical chart D2 with an imaging range image that is associated with the anatomical position for the medical image data. FIG. 12A shows an example in which when the pointer or cursor is placed at a coordinate, a local structure D4 that corresponds to the anatomical position that corresponds to the coordinate is popped up in a vicinity of the coordinate. In the example shown in FIG. 12A, the "apex of left lung" is displayed as the local structure that corresponds to the part indicted by an arrow. If the pointer or cursor is moved to a coordinate associated with another anatomical position, the popped-up local structure is replaced with a local structure that corresponds to the anatomical position that corresponds to the coordinate at which the pointer or cursor is placed.

The anatomical chart D2 with an imaging range image in which a local structure is displayed as described above may extend over a certain range of coordinates. For example, the anatomical chart D2 with an imaging range image may extend over a certain range of coordinates centered at the coordinate associated with the anatomical position of the anatomical chart D2. When the range of coordinates of an anatomical chart D2 with an imaging range image overlaps with the range of coordinates of another anatomical chart D2 with an imaging range image, the local structure for each range may be displayed, or the range of coordinates of the anatomical chart D2 may be reset so as not to overlap with the range of coordinates of the another anatomical chart D2.

Figure 12B:
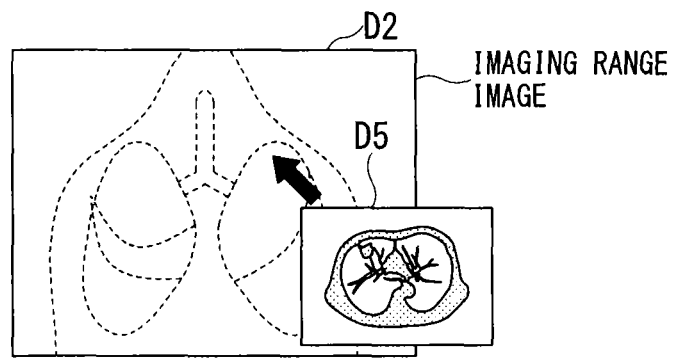
FIG. 12B shows a modification of the display example shown in FIG. 12A.

FIG. 12B shows a modification of the display example shown in FIG. 12A. While FIG. 12A shows an example in which a corresponding local structure is shown in text, FIG. 12B shows an example in which a thumbnail D5 of a corresponding slice image is popped up. The slice image that corresponds to the anatomical position is identified by the corresponding image identifying unit 36.

In the example shown in FIG. 12B, when the pointer or cursor is placed at the coordinate of the anatomical chart D2 with an imaging range image that is associated with an anatomical position for the medical image data currently being displayed, a slice image including the anatomical position is displayed as a thumbnail. As with FIG. 12A, FIG. 12B shows an example in which the cursor represented by an arrow is placed at the apex of the left lung, and a reduced-size slice image including the apex of the left lung (thumbnail image) D5 is displayed at a side of the arrow. Such a display allows the user to check whether the slice image is a desired slice image or not before a high-resolution slice image is actually displayed. In addition, such a display facilitates the user to search for a desired slice image.

Figure 13A:
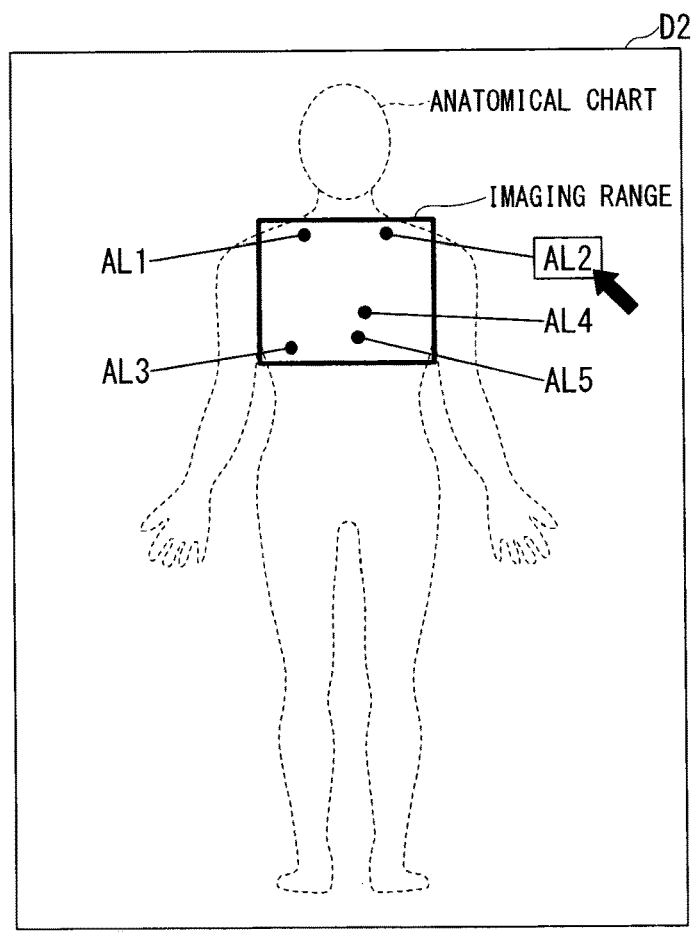
FIG. 13A shows an example of the anatomical chart D2 with an imaging range image generated by the mapping chart generating unit.

FIG. 13 are diagrams for illustrating a method of displaying a slice image from an anatomical chart with an imaging range image in the medical image processing apparatus 100 according to the first embodiment. FIG. 13A shows an example of the anatomical chart D2 with an imaging range image generated by the mapping chart generating unit 37. The anatomical chart D2 with an imaging range image is a mapping chart (mapping anatomical chart) on which an imaging range image is superimposed. As shown in FIG. 13A, on the anatomical chart D2 with an imaging range image, a coordinate of a local structure on the anatomical chart that is associated with an anatomical position for medical image data can be displayed as a graphic, such as a dot, a local structure, or an identifier of an anatomical position, for example.

The corresponding image identifying unit 36 can identify a corresponding slice image by reversely deriving a voxel coordinate for the medical image data that corresponds to the selected anatomical position based on selection of a point or a local structure shown in the anatomical chart D2 with an imaging range image.

Figure 13B:
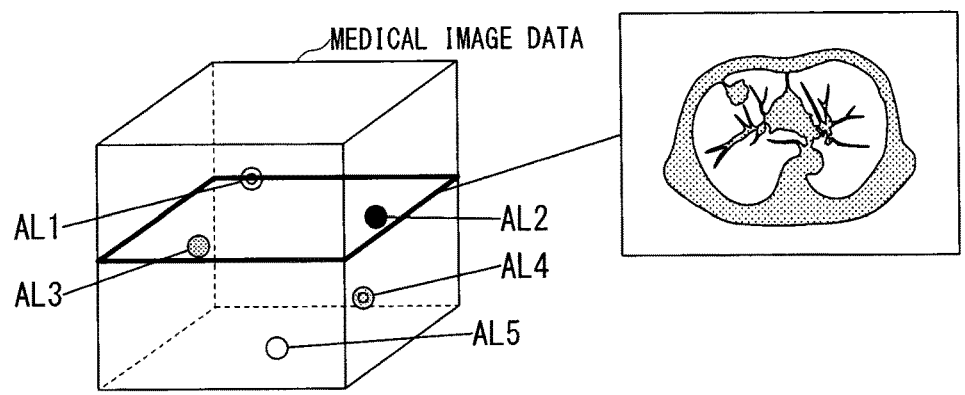
FIG. 13B shows medical image data from which the anatomical chart D2 with an imaging range image is generated, as an example.

For example, in the example shown in FIG. 13A, the anatomical position "AL2" is selected on the anatomical chart D2 with an imaging range image. FIG. 13B shows, as an example, medical image data from which the anatomical chart D2 with an imaging range image is generated. The anatomical position "AL2" selected in the example shown in FIG. 13A is included in the slice image shown by a solid frame in the medical image shown in FIG. 13B. In this way, the corresponding image identifying unit 36 can display a corresponding slice image selected from the medical image data according to the anatomical position selected on the anatomical chart D2 with an imaging range image.

The display examples described above with reference to FIGS. 10 to 13 allow the user to grasp the anatomical site included in the medical image data without actually displaying the medical image. In addition, the display examples facilitate the user to check at what anatomical position the slice image being currently displayed lies. Furthermore, by selecting an anatomical position displayed on the anatomical chart with an imaging range image, a content of a reference literature, an anatomical dictionary or the like that is associated with the anatomical position can be displayed. The reference literature, the anatomical dictionary or the like that is associated with the anatomical position may be stored in the storage unit 20 of the medical image processing apparatus 100 or stored in an external storage device. Alternatively, a description concerning the anatomical position may be searched for on the Internet, and the search result may be displayed.

As described above, the medical image processing apparatus according to this embodiment allows the user to grasp the anatomical site in the medical image based on the anatomical position without information such as study information. In addition, the medical image processing apparatus allows the user to easily grasp or examine the site or viscus in the medical image from the anatomical position. Furthermore, the user can quickly find a desired image because the user can select an anatomical position in the anatomical chart with an imaging range image and instantaneously move to a slice image that corresponds to the selected anatomical position.

Second Embodiment

A second embodiment relates to selection and display of medical image data with an annotation imparted thereto in addition to the first embodiment.

An annotation is displayed to indicate a part to be observed with care on a key image, which is an image determined by a radiologist as a key for radiological interpretation, from among a plurality of images included in one piece of medical image data in creation of a radiological interpretation report. The annotation is displayed as a symbol, such as an arrow, or a line enclosing a region on the key image. According to the second embodiment, the position information identifying unit 35 identifies the position of the annotation, which is a part of interest of the medical image, on the mapping chart.

Figure 14:
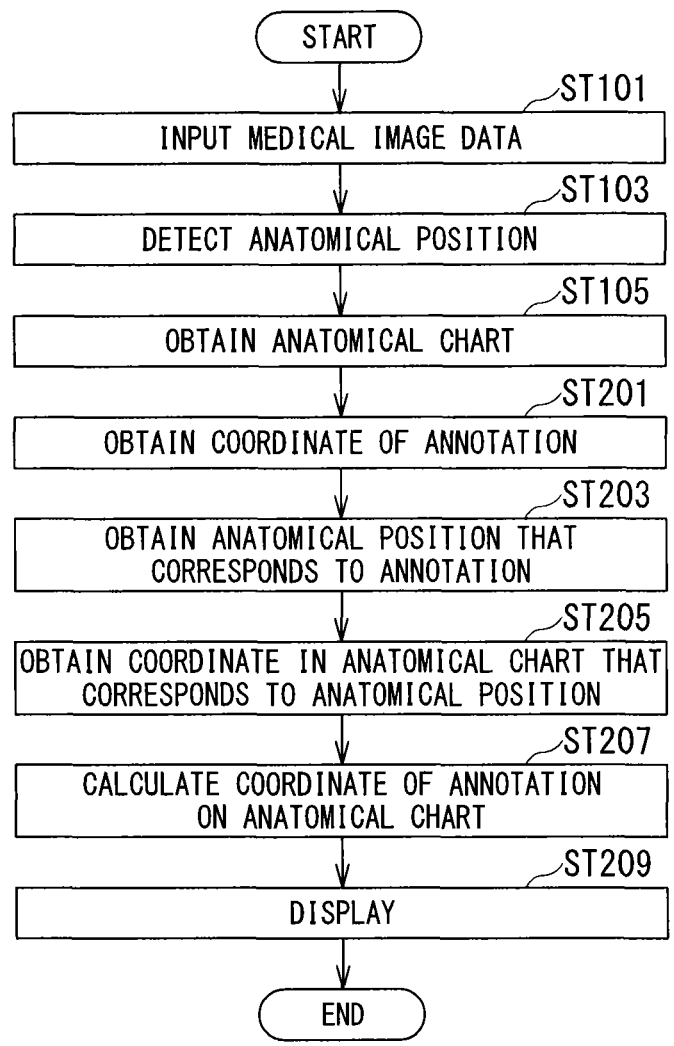
FIG. 14 is a flowchart showing an example of an operation of a medical image processing apparatus according to the second embodiment.

FIG. 14 is a flowchart showing an example of an operation of a medical image processing apparatus 100 according to the second embodiment. The same processings as those in the first embodiment shown in FIG. 3 are denoted by the same reference numerals, and redundant description thereof will be omitted. The configuration of the medical image processing apparatus 100 according to the second embodiment is the same as the medical image processing apparatus 100 according to the first embodiment shown in FIG. 2.

In ST201, the position information identifying unit 35 obtains a voxel coordinate of the annotation imparted to the medical image data.

In ST203, the position information identifying unit 35 identifies at least one anatomical position that corresponds to the annotation imparted to the medical image data from among positions (anatomical positions) of local structures detected for the medical image data and obtains a voxel coordinate of the anatomical position.

In ST205, the position information identifying unit 35 obtains a coordinate on the anatomical chart that corresponds to the anatomical position identified for the annotation.

In ST207, the position information identifying unit 35 calculates a coordinate on the anatomical chart that corresponds to the voxel coordinate of the annotation from the voxel coordinate of the anatomical position that corresponds to the annotation and the coordinate on the anatomical chart.

In ST209, the mapping chart generating unit 37 generates a mapping chart by attaching a mark that represents the position of the annotation to the coordinate on the anatomical chart that corresponds to the voxel coordinate of the annotation, and makes the display unit 40 display the mapping chart.

Figures 15A, 15B:
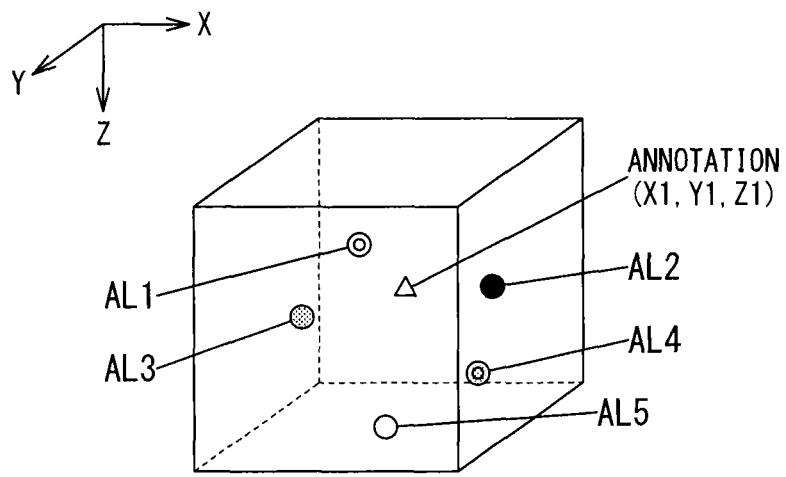
FIG. 15A shows medical image data input to the medical image processing apparatus.
FIG. 15B shows an example of a list of anatomical positions in a vicinity of the annotation whose coordinates are identified.

FIG. 15 are diagrams for illustrating an annotation included in medical image for the medical image processing apparatus 100 according to the second embodiment. As with FIG. 7A, FIG. 15A shows medical image data input to the medical image processing apparatus 100. In the example shown in FIG. 15A, as in FIG. 7A, five anatomical positions "AL1", "AL2", "AL3", "AL4" and "AL5" are detected for the medical image data. The position information identifying unit 35 identifies voxel coordinates (X1, "Y1", "Z1") of the annotation indicated by a triangle in the medical image data (ST201).

FIG. 15B shows an example of a list of anatomical positions in a vicinity of the annotation whose coordinates are identified. As illustrated in FIG. 15A, five anatomical positions are detected in the medical image data. In the example shown in FIG. 15B, of these anatomical positions, the four anatomical positions "AL1", "AL2", "AL3" and "AL4" are shown as anatomical positions that correspond to the annotation. In the example shown in FIG. 15B, voxel coordinates of the anatomical position "AL1" are (Xa1, Ya1, Za1), voxel coordinates of the anatomical position "AL2" are (Xa2, Ya2, Za2), voxel coordinates of the anatomical position "AL3" are (Xa3, Ya3, Za3), and voxel coordinates of the anatomical position "AL4" are (Xa4, Ya4, Za4).

The position information identifying unit 35 can obtain a coordinate on the anatomical chart that corresponds to an anatomical position on each medical image identified for an annotation. For example, as shown in FIG. 8B, coordinates on the anatomical chart that correspond to the anatomical positions "AL1", "AL2", "AL3" and "AL4" are (Xb1, Yb1), (Xb2, Yb2), (Xb3, Yb3) and (Xb4, Yb4), respectively. The position information identifying unit 35 can obtain both the coordinate of an anatomical position in the medical image data and the coordinate of a corresponding anatomical position in the anatomical chart (ST203, ST205).

Figure 16:
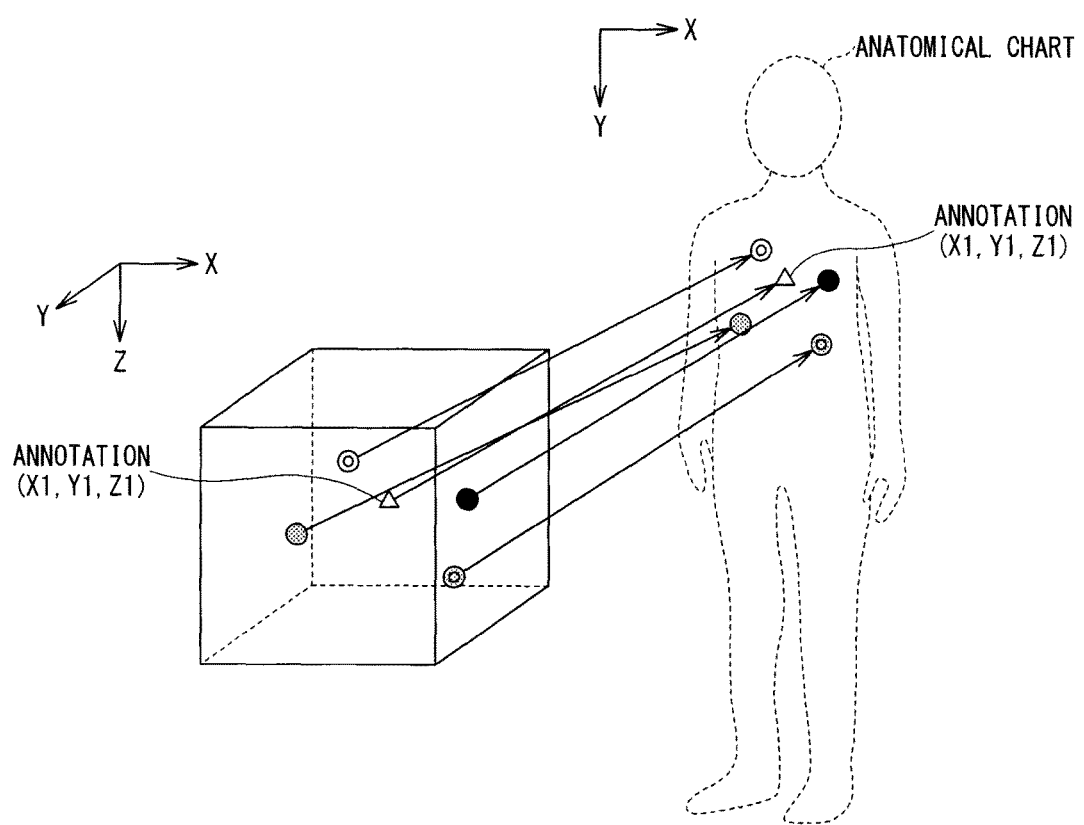
FIG. 16 is a diagram for illustrating a method of calculating a coordinate on the anatomical chart of an annotation included in a medical image for the medical image processing apparatus according to the second embodiment.

FIG. 16 is a diagram for illustrating a method of calculating a coordinate on the anatomical chart of an annotation included in a medical image for the medical image processing apparatus 100 according to the second embodiment. FIG. 16 shows an example in which anatomical positions included in the medical image data are projected to corresponding coordinates in the anatomical chart. In this way, coordinates of anatomical positions related to the annotation in the medical image data can be associated with coordinates on the anatomical chart to determine a relationship between the coordinates in the medical image data and the coordinates on the anatomical chart, thereby calculating coordinates of the annotation imparted to the medical image data. More specifically, coordinates (Xi, Yi) of the annotation on the anatomical chart can be calculated from voxel coordinates (X1, Y1, Z1) of the annotation imparted to the medical image data by calculating a projection matrix P shown below.

[Expression 1]

$$\begin{pmatrix} X1a & Y1a & Z1a1 \\ X2a & Y2a & Z2a1 \\ X3a & Y3a & Z3a1 \\ X4a & Y4a & Z4a1 \end{pmatrix} \times P = \begin{pmatrix} X1b & Y1b \\ X2b & Y2b \\ X3b & Y3b \\ X4b & Y4b \end{pmatrix} \quad (1)$$

According to the projection matrix P determined according to the formula (1) shown above, the coordinates (Xi, Yi) of the annotation on the anatomical chart can be determined according to (X1, Y1, Z1, 1)×P=(Xi, Yi) (ST207).

Based on the coordinates of the annotation on the anatomical chart identified as described above, the mapping chart generating unit 37 generates a mapping chart by adding a mark that represents the position of the annotation at the coordinates on the anatomical chart that correspond to the voxel coordinates of the annotation, and makes the display unit 40 display the mapping chart (ST209). The mapping chart may be an anatomical chart with an annotation, which is an anatomical chart with an imaging range image to which an annotation is added.

Although the coordinates of the annotation on the anatomical chart are calculated from the projection matrix P using anatomical positions in a vicinity of the annotation in the above description, the anatomical positions used for calculation of the projection matrix P may be selected based on the reliability of the anatomical positions. Alternatively, the anatomical positions to be used may be selected from a viscus or site to which the anatomical position closest to the annotation belongs, or the anatomical positions to be used may be selected based on a viscus or site to be inspected known from the study information.

Although four selected points are used to calculate the projection matrix P in the coordinate transformation in the example described above, five or more anatomical positions may be used to perform a coordinate transformation by non-rigid registration. The coordinate transformation by non-rigid registration is a registration method that involves a deformation and can associate two sets of a plurality of coordinates with each other. If the coordinate transformation by non-rigid registration is used, the medical image can be smoothly deformed to make all the selected anatomical positions agree with the corresponding coordinates on the anatomical chart, so that the coordinates can be more precisely aligned with each other. The coordinates of the annotation may be transformed by using the coordinate transformation by non-rigid registration. For example, if the anatomical chart is two-dimensional, precise alignment of the coordinates on the anatomical chart and the anatomical positions on the medical image can be performed by first preparing a three-dimensional anatomical chart and then deforming the medical image by non-rigid registration in such a manner that the coordinates of the local structure on the three-dimensional anatomical chart agree with the corresponding anatomical positions on the medical image. Then, the coordinates that correspond to the annotation coordinates specified in the medical image can be identified on the three-dimensional anatomical chart, and the identified coordinates of the annotation can be projected onto the two-dimensional anatomical chart. In the non-rigid registration, all the anatomical positions may be used, or only the anatomical positions related to the annotation may be used.

In the following, display examples of the anatomical chart with an annotation will be described with reference to FIGS. 17 to 19. As in the first embodiment, the medical image processing apparatus 100 selects a medical image for radiological interpretation or controls movement to a slice image that corresponds to the annotation selected in the medical image. The anatomical chart with an annotation may include a function of the anatomical chart with an imaging range image described above with reference to the first embodiment.

Figure 17:
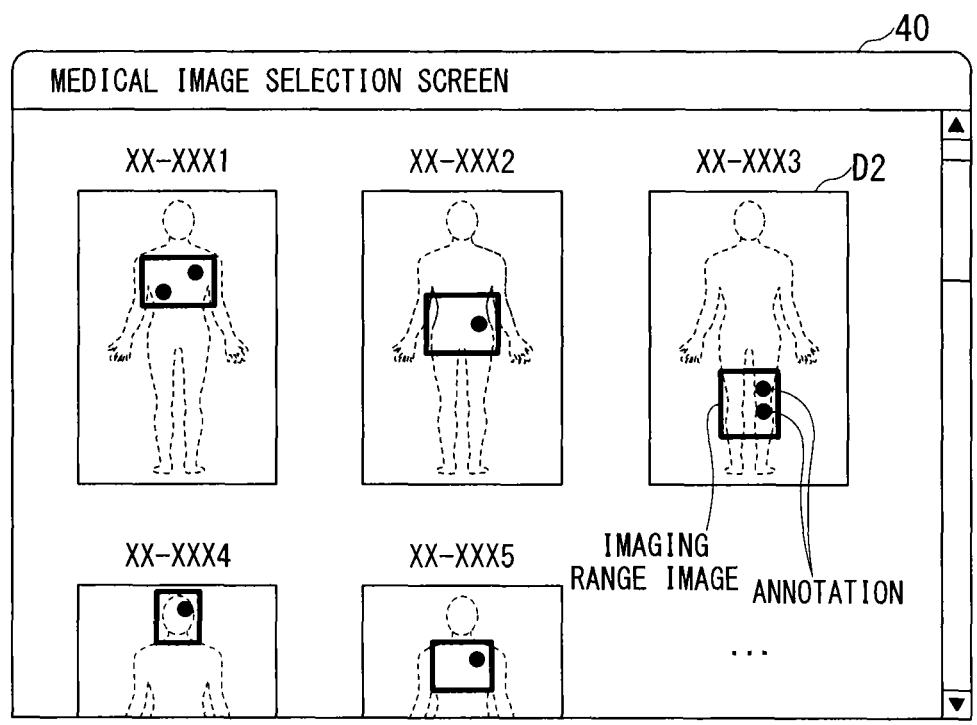
FIG. 17 is a diagram for illustrating an example of how the annotation is displayed when a medical image is selected in the medical image processing apparatus according to the second embodiment.

FIG. 17 is a diagram for illustrating an example of how the annotation is displayed when a medical image is selected in the medical image processing apparatus 100 according to the second embodiment. As with FIG. 10, FIG. 17 shows an example of how the annotation is displayed when medical image data for which a radiological interpretation report is created is selected from among input medical image data.

A radiological interpretation report can be created by performing identification of a key image and imparting of an annotation on a medical image display device or the like and then entering the image and a finding. As an alternative, after radiological interpretation and entry of a finding are completed, a radiological interpretation report may be created by compiling the finding, the key image and the annotation. In the latter case, the key image and the medical image with the annotation are input to the medical image processing apparatus 100.

As in FIG. 10, in the example shown in FIG. 17, the input medical image is represented by an icon of an anatomical chart D2 with an annotation. The anatomical chart D2 with an annotation shown in FIG. 17 includes an imaging range image and an annotation. As shown in the example shown in FIG. 17, a plurality of annotations may be set for one medical image. Although annotations in the medical image of a study ID "XX-XXX1" in FIG. 17 are represented by circles, annotations may be represented by other graphics, such as a rectangular, a star or an arrow. Alternatively, an annotation may be displayed by enclosing a certain region centered at the coordinate of the annotation identified on the anatomical chart or by highlighting the annotation in a different color. Alternatively, a graphic or the like that represents the annotation may be animation that blinks, for example. Furthermore, an anatomical position in a vicinity of the annotation may be displayed at the same time.

Figure 18:
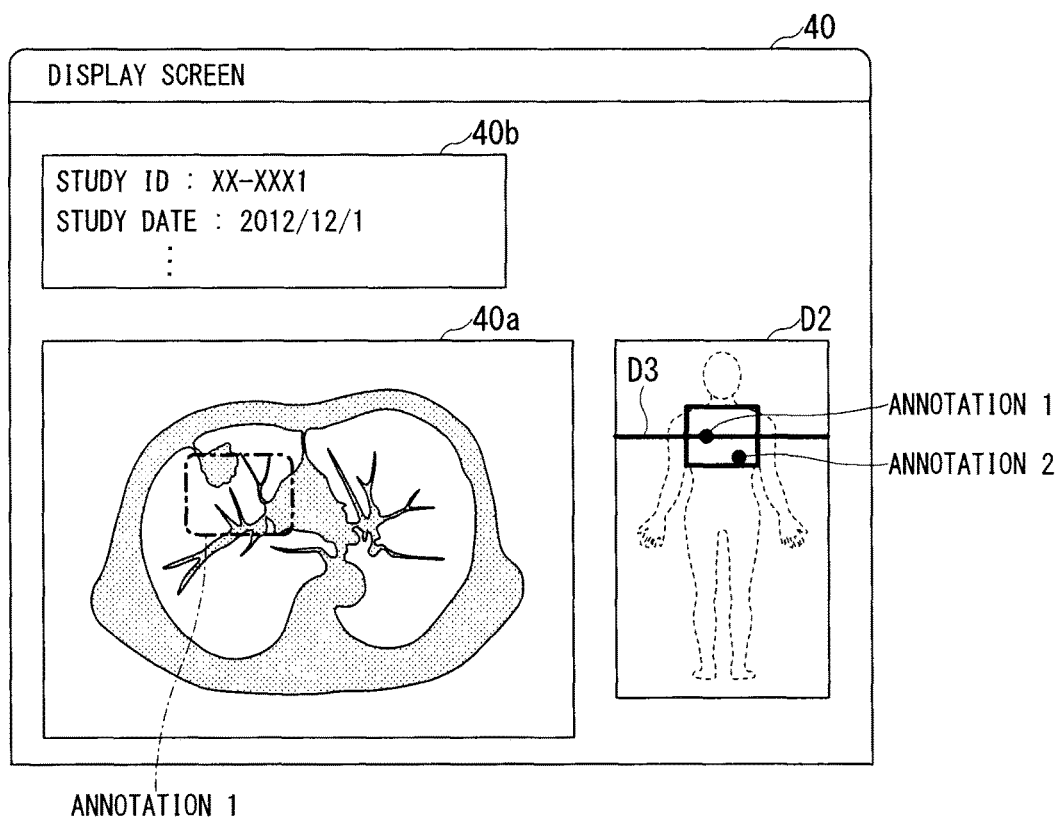
FIG. 18 is a diagram for illustrating an example of how an annotation is displayed in a display of a medical image on the medical image processing apparatus according to the second embodiment.

FIG. 18 is a diagram for illustrating an example of how an annotation is displayed in a display of a medical image on the medical image processing apparatus 100 according to the second embodiment. As with FIG. 11, FIG. 18 shows an example in which the slice image 40a included in the medical image data that is a target of radiological interpretation is displayed on the display unit 40.

In the slice image 40a shown in FIG. 18, an annotation 1 enclosed by an alternate long and short dash line is displayed. The annotation 1 is also displayed on the anatomical chart D2 with an annotation at the position of the indicator D3 that indicates the position of the slice image being currently displayed. On the anatomical chart D2 with an annotation in FIG. 18, an annotation 2 is also displayed. If the display screen is touched and pressed at the coordinate of the annotation 2 in the anatomical chart D2 with an annotation in FIG. 18, for example, the slice image can be instantaneously replaced with the slice image with the annotation 2 shown in FIG. 19.

Figure 19:
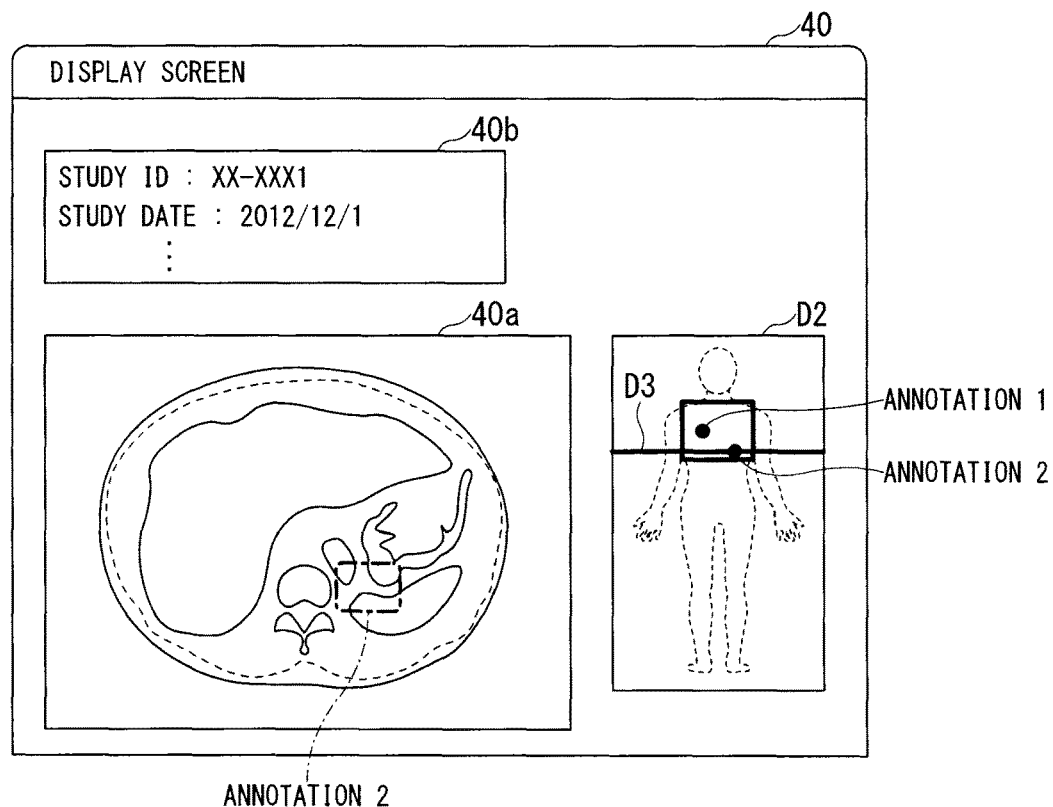
FIG. 19 is a diagram for illustrating an example of the display after the annotation 2 is selected in the display shown in FIG. 18 on the medical image processing apparatus according to the second embodiment.

FIG. 19 is a diagram for illustrating an example of the display after the annotation 2 is selected in the display shown in FIG. 18 on the medical image processing apparatus 100 according to the second embodiment. As with FIGS. 11 and 18, FIG. 19 shows an example in which the slice image 40a included in the medical image data that is a target of radiological interpretation is displayed on the display unit 40.

The slice image 40a shown in FIG. 19 is different from the slice image shown in FIG. 18. In the slice image 40a shown in FIG. 19, the annotation 2 enclosed by an alternate long and short dash line is displayed. The position of the indicator D3 on the anatomical chart D2 with an annotation is different from the position of the annotation 2.

Thus, in the example shown in FIG. 17, the position of the annotation can be grasped without displaying the medical image, and therefore, the target for which a radiological interpretation report is to be created can be easily selected. In the examples shown in FIGS. 18 and 19, the medical image with the annotation can be easily searched for while entering a finding or the like. In addition, since the anatomical chart with an imaging range image is associated with anatomical positions, a relationship between the position of the annotation and anatomical positions around the position of the annotation can be easily grasped.

Third Embodiment

A third embodiment relates to generation and display of position information on a coordinate specified on a medical image or an anatomical chart with an annotation in addition to the first and second embodiments. More specifically, the position information identifying unit 35 calculates position information that indicates a distance, a direction or the like from an anatomical position to an annotation or a selected coordinate on a medical image based on the anatomical position.

Figure 20:
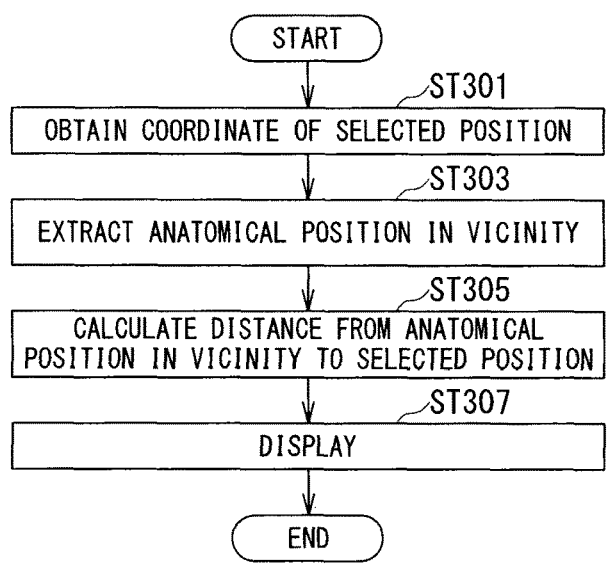
FIG. 20 is a flowchart showing an example of an operation of a medical image processing apparatus according to a third embodiment.

FIG. 20 is a flowchart showing an example of an operation of a medical image processing apparatus 100 according to a third embodiment. The configuration of the medical image processing apparatus 100 according to the third embodiment is the same as the medical image processing apparatus 100 according to the first embodiment shown in FIG. 2. The third embodiment relates to an operation after the anatomical chart with an anatomical position described above with reference to the first embodiment or the anatomical chart with an annotation described above with reference to the second embodiment is generated.

In ST301, the position information identifying unit 35 obtains a coordinate of a selected position in a slice image or an anatomical chart with an annotation input via the input unit 50 provided with a mouse or the like. The selected position in the slice image is a coordinate in the slice image at which the pointer or cursor is placed input via the input unit 50 provided with a mouse or the like. Similarly, the selected position in the anatomical chart with an annotation is a coordinate in the anatomical chart with an annotation at which the pointer or cursor is placed input via the input unit 50. For example, the selected position may be the coordinate of an annotation displayed in the anatomical chart with an annotation or the coordinate of an anatomical position in the anatomical chart with an annotation. The position information identifying unit 35 can obtain a voxel coordinate in a corresponding medical image from the coordinate of the annotation or anatomical position in the anatomical chart with an annotation. The annotation and the anatomical position are retained in a state where the voxel coordinate in the medical image and the coordinate on the anatomical chart with an annotation are associated with each other.

In ST303, the position information identifying unit 35 identifies an anatomical position in a vicinity of the selected position from the obtained voxel coordinate.

In ST305, the position information identifying unit 35 calculates a distance and a direction from the identified anatomical position in the vicinity to the coordinate of the selected position.

In ST307, the display unit 40 displays the calculated distance and direction.

Figure 21:
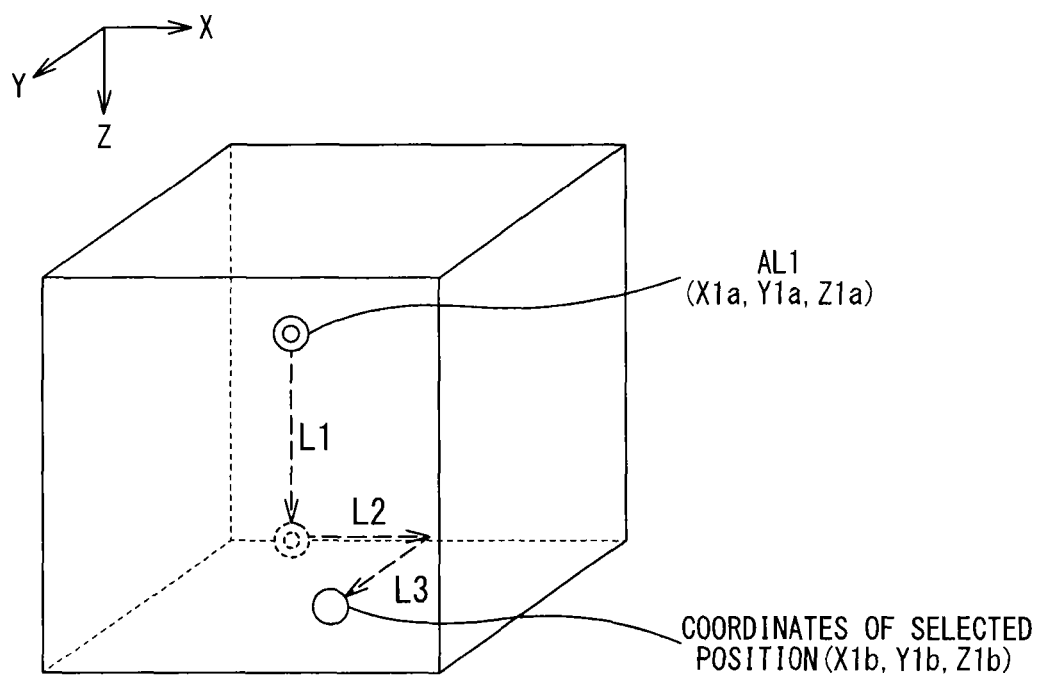
FIG. 21 is a diagram for illustrating a method of calculating a distance from an anatomical position to a selected position in the medical image processing apparatus according to the third embodiment.

FIG. 21 is a diagram for illustrating a method of calculating a distance from an anatomical position to a selected position in the medical image processing apparatus 100 according to the third embodiment. FIG. 21 shows an example in which the anatomical position "AL1" is identified as an anatomical position in a vicinity of the coordinate of the selected position.

As shown in FIG. 21, the coordinates of the anatomical position "AL1" are (X1a, Y1a, Z1a), and the coordinates of the selected position are (X1b, Y1b, Z1b).

Reference symbol "L1" shown in FIG. 21 represents a distance between a Z coordinate of the anatomical position "AL1" and a Z coordinate of the selected position. The distance from the coordinate of the anatomical position "AL1" to the coordinate of the selected position can be calculated from a voxel size (ST305). Similarly, reference symbol "L2" represents a distance between an X coordinate of the anatomical position "AL1" and an X coordinate of the selected position. Similarly, reference symbol "L3" represents a distance in the Y-axis direction.

A plurality of the distances and directions calculated as described above can be combined to express the selected position as being at a distance of "Δ mm from the anatomical position "AL1" in the foot direction, ○ mm from the anatomical position "AL1" in the right direction and □ mm from the anatomical position "AL1" in the ventral direction".

FIG. 22 are diagrams for illustrating first display examples of the distance from an anatomical position to a selected position in the medical image processing apparatus 100 according to the third embodiment. FIG. 22 show examples in which a selected position is set in the slice image 40a displayed on the display unit 40. Once a selected position is set in the slice image 40a, the position information identifying unit 35 obtains a coordinate of the position from the medical image data. From the obtained coordinate, the position information identifying unit 35 calculates a distance and direction from an anatomical position in a vicinity thereof as shown in FIG. 21 (ST305).

Figure 22A:
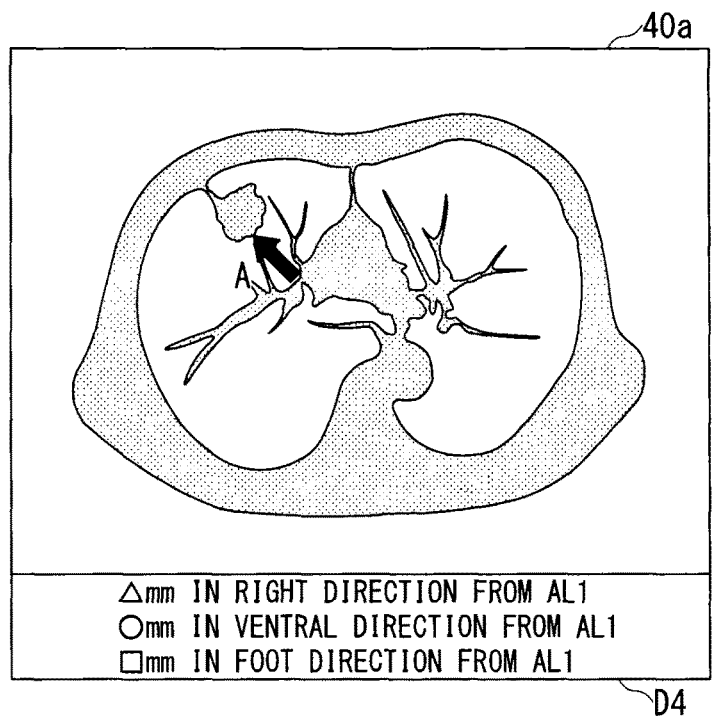
FIG. 22A shows an example in which position information on the calculated selected position is displayed in a position information display region D4 below the slice image.

FIG. 22A shows an example in which position information on the calculated selected position is displayed in a position information display region D4 below the slice image 40a. In the example shown in FIG. 22A, the position of an arrow A in the slice image 40a is selected as a selected position, and it reads in the position information display region D4 that "Δ mm from AL1 in right direction, ○ mm in ventral direction and □ mm in foot direction". In this way, position information identifying unit 35 calculates the position of the coordinate selected on the slice image from the anatomical position in the vicinity and displays the position.

Although FIG. 22A shows an example in which position information on one anatomical position is displayed in the position information display region D4, a plurality of pieces of position information on a plurality of anatomical positions may be displayed. The anatomical position for which the position information is to be calculated may be selected depending on the reliability of the anatomical position information. Furthermore, a plurality of pieces of position information may be displayed in the position information display region D4 shown in FIG. 22A in descending order of the reliability of the anatomical position information. Furthermore, a viscus or the like that corresponds to the selected position may be identified from the closest anatomical position or study information, and position information on the position form an anatomical position that relates to the viscus or the like may be calculated.

Figure 22B:
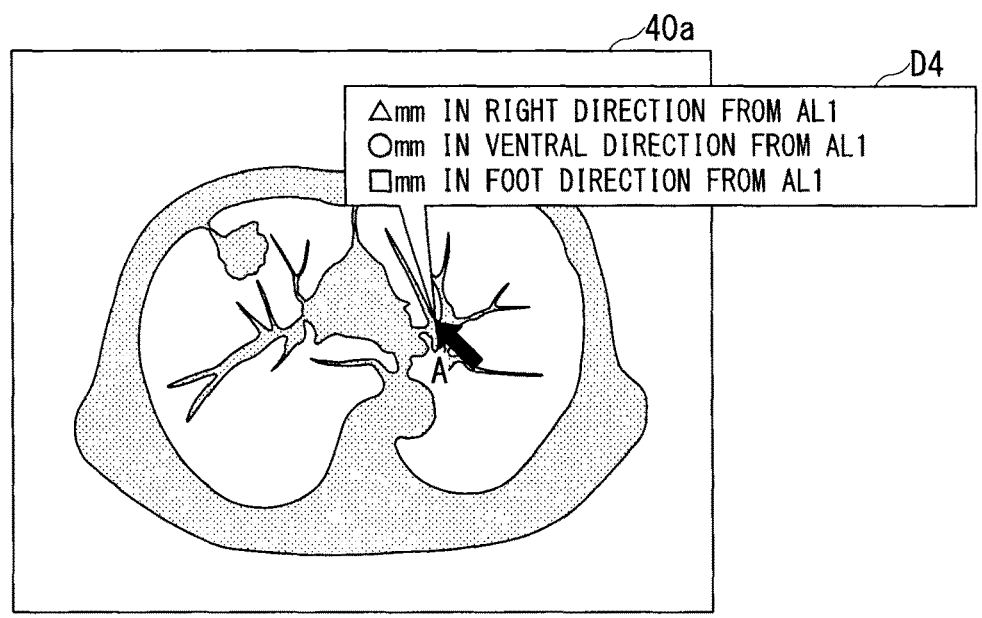
FIG. 22B shows a modification of the display example shown in FIG. 22A.

FIG. 22B shows a modification of the display example shown in FIG. 22A. While FIG. 22A shows an example in which the position information display region D4 is fixed below the slice image 40a, FIG. 22B shows an example in which the position information display region D4 is displayed in association with the arrow A that points at the selected position. In the example shown in FIG. 22B, the position information display region D4 is displayed in the form of a balloon. The balloon originates at the coordinate of the selected position pointed by the arrow A.

In this way, if the distance or direction from an anatomical position in the vicinity thereof, an annotation can be imparted to any position on the slice image simply by specifying the coordinate of the position, and the position of the annotation can be precisely described when a finding is entered to a radiological interpretation report. In addition, if position information on a plurality of anatomical positions is displayed, the selected position can be there-dimensionally grasped even if the slice image is two-dimensional.

FIG. 23 are diagrams for illustrating second display examples of a distance from an anatomical position to a selected position in the medical image processing apparatus 100 according to the third embodiment. While FIG. 21 shows an example in which a coordinate on the slice image is selected as a selected position, FIG. 23 show examples in which a coordinate that corresponds to an annotation on the anatomical chart with an annotation is selected as a selected position. The selected position may be a coordinate or local structure that corresponds to an anatomical position.

Figure 23A:
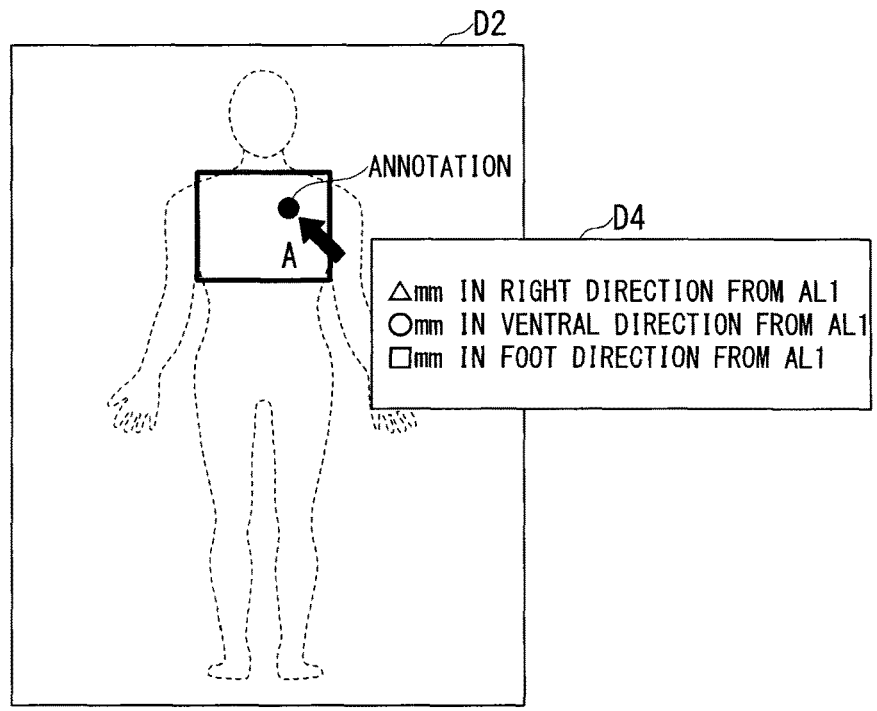
FIG. 23A shows an example in which the calculated distance and direction to the anatomical position is displayed in a vicinity of the arrow A.

In the example shown in FIG. 23A, the position information identifying unit 35 identifies a voxel coordinate of the annotation specified as the selected position pointed by the arrow A as the coordinate of the selected position, and calculates a distance and direction from the voxel coordinate to an anatomical position in a vicinity thereof. FIG. 23A shows an example in which the calculated distance and direction to the anatomical position is displayed in a vicinity of the arrow A.

Figure 23B:
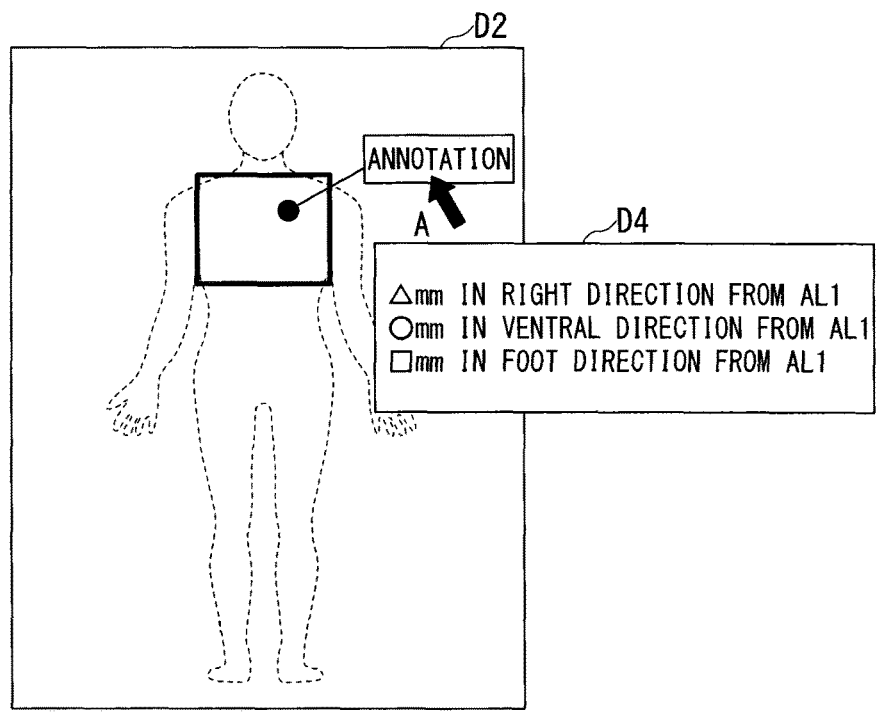
FIG. 23B shows a modification of the example shown in FIG. 23A.

FIG. 23B shows a modification of the example shown in FIG. 23A. FIG. 23B shows an example in which a label of an annotation displayed on the anatomical chart with an annotation is selected with the arrow A, and the calculated distance and direction to the anatomical position are displayed in a vicinity of the label of the annotation selected with the arrow A.

As described above, the position of the annotation found in the finding can be easily described by displaying the position information on the annotation on the anatomical chart or the position of a local structure on the anatomical chart. Furthermore, information that is more appropriate as the position information on the annotation can be easily found by simply selecting an anatomical position on the anatomical chart with an annotation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus that displays a medical image of an object, comprising:
   a medical image input processor configured to obtain the medical image from a modality device;
   a position detecting processor configured to detect anatomical points out of a group of anatomical points from the medical image depicting the inside of the object and determine coordinates in a patient or voxel coordinate system of each of the anatomical points, by using a model for defining the group of anatomical points, the determined coordinates of the each of the anatomical points representing an anatomical position on a corresponding local structure in a human body;
   a human body chart memory configured to store a human body chart that represents the human body, wherein, on the human body chart, an anatomical chart coordinate system associated with each point of the group of anatomical points is defined;
   a mapping chart generating processor configured to associate the determined coordinates of the each of the anatomical points in the patient or voxel coordinate system with coordinates in the anatomical chart coordinate system, to generate an imaging range image that indicates an imaging range of the medical image on the human body chart based on the anatomical chart coordinates of the each of the anatomical points detected from the medical image, and to generate a mapping chart that is the human body chart on which the imaging range image is superimposed; and
   a display configured to display the mapping chart.

2. The medical image processing apparatus according to claim 1, wherein the display displays a list of a plurality of mapping chart that correspond to a plurality of medical images in a selectable display format.

3. The medical image processing apparatus according to claim 1, wherein the mapping chart generating processor generates a mapping chart that is the human body chart to which a mark that indicates a position of an annotation imparted to the medical image is added.

4. The medical image processing apparatus according to claim 3, wherein the mapping chart generating processor generates the mapping chart by adding the mark that indicates the position of the local structure and the mark that indicates the position of the annotation imparted to the medical image to the human body chart.

5. The medical image processing apparatus according to claim 1, wherein the mapping chart generating processor generates the mapping chart by adding at least one of the mark that indicates the position of the local structure and the mark that indicates the position of the annotation imparted to the medical image to the human body chart, and superimposing the imaging range image on the human body chart.

6. The medical image processing apparatus according to claim 1, wherein the mapping chart generating processor generates, for each of a plurality of medical images, an imaging range image that indicates an imaging range of the each of the plurality of medical images.

7. The medical image processing apparatus according to claim 1, wherein the mapping chart generating processor generates the imaging range image that includes all coordinates on the human body chart that correspond to positions of the local structure detected in the medical image.

8. The medical image processing apparatus according to claim 1, wherein the mapping chart generating processor generates an imaging range image whose opposite ends in a predetermined direction are defined by a maximum coordinate and a minimum coordinate in the predetermined direction on the human body chart that correspond to positions of the local structure detected from the medical image.

9. The medical image processing apparatus according to claim 1, further comprising:
an position information identifying processor configured to identify a position of an annotation on the human body chart based on a coordinate of the annotation imparted to the medical image and the position of the local structure detected by the position detecting unit,
wherein the mapping chart generating processor adds a mark that indicates the position of the annotation to the mapping chart based on the position of the annotation on the human body chart identified by the position information identifying processor.

10. The medical image processing apparatus according to claim 9, wherein the position information identifying processor determines position information on the annotation based on the position of the local structure detected in the medical image, and
the mapping chart generating processor generates an image indicating the position information on the annotation and makes the display display the image.

11. The medical image processing apparatus according to claim 10, wherein the position information on the annotation includes information on a local structure in vicinity of the annotation and on a distance and direction from the local structure.

12. The medical image processing apparatus according to claim 10, wherein the position information identifying processor determines the position information on the annotation based on a projection matrix that represents a relationship between the coordinate of the annotation imparted to the medical image and a coordinate on the mapping chart.

13. The medical image processing apparatus according to claim 1, further comprising:
a corresponding image identifying processor configured to identify a sub-image, that corresponds to a position of the local structure selected from among positions of the local structures included in the mapping chart, from among a plurality of sub-images comprising the medial image, and make the display display the identified sub-image.

14. The medical image processing apparatus according to claim 1, further comprising:
a corresponding image identifying processor configured to identify, when a mark that indicates the position of the annotation is added to the mapping chart, a sub-image that corresponds to the position of the annotation from among a plurality of sub-images comprising the medical image, and make the display display the identified sub-image.

15. A medical image processing apparatus that displays a medical image of an object, comprising:
a medical image input processor configured to obtain the medical image from a modality device;
a position detecting processor configured to detect anatomical points out of a group of anatomical points from the medical image depicting the inside of the object and determine coordinates in a patient or voxel coordinate system of each of the anatomical points, by using a model for defining the group of anatomical points, the determined coordinates of the each of the anatomical points representing an anatomical position on a corresponding local structure in a human body;
a mapping chart generating processor configured to generate an imaging range image that indicates an imaging range of the medical image on the human body chart based on anatomical chart coordinates of the each of the anatomical points detected from the medical image, and to generate a mapping chart that is a human body chart on which the imaging range image is superimposed, wherein, on the human body chart, the anatomical chart coordinate system associated with each point of the group of anatomical points is defined, and to associate the determined coordinates of the each of the anatomical points in the patient or voxel coordinate system with coordinates in the anatomical chart coordinate system; and
a display configured to display the mapping chart.

16. A medical image processing system that obtains a medical image of an object through network and displays the medical image, comprising:
a medical image input processor configured to obtain the medical image from a modality device;
a position detecting processor configured to detect anatomical points out of a group of anatomical points from the medical image depicting the inside of the object and determine coordinates in a patient or voxel coordinate system of each of the anatomical points, by using a model for defining the group of anatomical points, the determined coordinates of the each of the anatomical points representing an anatomical position on a corresponding local structure in a human body;
a human body chart memory configured to store a human body chart that represents the human body, wherein, on the human body chart, an anatomical chart coordinate system associated with each point of the group of anatomical points is defined;
a mapping chart generating processor configured to associate the determined coordinates of the each of the anatomical points in the patient or voxel coordinate system with coordinates in the anatomical chart coordinate system, to generate an imaging range image that indicates an imaging range of the medical image on the human body chart based on the anatomical chart coordinates of the each of the anatomical points detected from the medical image, and to generate a mapping chart that is the human body chart on which the imaging range image is superimposed; and
a display configured to display the mapping chart.

17. The medical image processing apparatus according to claim 1, wherein the mapping chart generating processor generates a mapping chart that is the human body chart to which a mark indicating the plurality of positions of the characteristic local structures detected by the position detecting processor is added.

\* \* \* \* \*